(12) United States Patent
Shishido et al.

(10) Patent No.: US 10,471,141 B2
(45) Date of Patent: Nov. 12, 2019

(54) BISPHOSPHONATE-CONTAINING VACCINE PHARMACEUTICAL COMPOSITION FOR HUMORAL IMMUNITY

(71) Applicant: NITTO DENKO CORPORATION, Osaka (JP)

(72) Inventors: Takuya Shishido, Osaka (JP); Daisuke Asari, Osaka (JP); Mitsuhiko Hori, Osaka (JP)

(73) Assignee: NITTO DENKO CORPORATION, Osaka (JP)

( * ) Notice: Subject to any disclaimer, the term of this patent is extended or adjusted under 35 U.S.C. 154(b) by 0 days.

(21) Appl. No.: 15/507,525

(22) PCT Filed: Sep. 2, 2015

(86) PCT No.: PCT/JP2015/074921
§ 371 (c)(1),
(2) Date: Feb. 28, 2017

(87) PCT Pub. No.: WO2016/035809
PCT Pub. Date: Mar. 10, 2016

(65) Prior Publication Data
US 2017/0281759 A1    Oct. 5, 2017

(30) Foreign Application Priority Data

Sep. 3, 2014 (JP) ................... 2014-179124

(51) Int. Cl.
| | | |
|---|---|---|
| *A61K 38/00* | (2006.01) | |
| *A61K 39/00* | (2006.01) | |
| *A61K 39/395* | (2006.01) | |
| *C07K 16/28* | (2006.01) | |
| *A61K 31/198* | (2006.01) | |
| *A61K 39/39* | (2006.01) | |
| *A61K 31/663* | (2006.01) | |
| *A61K 47/54* | (2017.01) | |

(52) U.S. Cl.
CPC .......... *A61K 39/395* (2013.01); *A61K 31/663* (2013.01); *A61K 39/00* (2013.01); *A61K 39/39* (2013.01); *A61K 47/548* (2017.08); *A61K 2039/55511* (2013.01); *A61K 2039/58* (2013.01)

(58) Field of Classification Search
CPC ................ A61K 39/3955; A61K 45/06; C07K 16/2896; C07K 2317/21; C07K 2317/34
See application file for complete search history.

(56) References Cited

U.S. PATENT DOCUMENTS

| | | | |
|---|---|---|---|
| 6,740,325 B1 | 5/2004 | Arnon et al. | |
| 2007/0190169 A1 | 8/2007 | Nieda et al. | |
| 2008/0112974 A1 | 5/2008 | Czerkinsky et al. | |
| 2008/0193487 A1 | 8/2008 | Schild et al. | |
| 2009/0104161 A1 | 4/2009 | Nieda et al. | |
| 2012/0156280 A1 | 6/2012 | Dow et al. | |
| 2013/0309270 A1* | 11/2013 | von Andrian | A61K 39/00 424/277.1 |

FOREIGN PATENT DOCUMENTS

| | | | |
|---|---|---|---|
| CN | 103768595 | A | 5/2014 |
| CN | 103768595 | * | 7/2014 |
| EP | 3 189 854 | A1 | 7/2017 |
| JP | 2002-531415 | A | 9/2002 |
| JP | 2010-259373 | A | 11/2010 |
| WO | 2006/006638 | A1 | 1/2006 |
| WO | 2007/029689 | A1 | 3/2007 |
| WO | 2011/116299 | A2 | 9/2011 |
| WO | 2012/054807 | A2 | 4/2012 |

OTHER PUBLICATIONS

Tonti et al., Bisphophonates target B cells to enhance humoral immune responses, 2013, Cell Reports, 5:323-330.*
Tonti et al., "Bisphosphonates Target B cells to enhance humoral immune responses", Cell Reports, 2013, 5:323-330.*
Prausnitz et al., "Transdermal drug delivery", Nat Biotechnol, 2008, 26(11): 1261-1268.*
Hidemasa Katsumi et al., "Efficient Transdermal Delivery of Alendronate, a Nitrogen-Containing Bisphosphonate, Using Tip-Loaded Self-Dissolving Microneedle Arrays for the Treatment of Osteoporosis"; Pharmaceutics, vol. 9, No. 3; Aug. 17, 2017, pp. 29, XP055436827.
Elizabeth Acosta-Ramirez et al., "Respiratory macrophages regulate CD4 T memory responses to mucosal immunization with recombinant adenovirus-based vaccines"; Cellular Immunology, vol. 310; Jul. 12, 2016; pp. 53-62.
Extended European Search Report issued in Patent Application No. 15837618.6, dated Jan. 17, 2018.
Akihiro Hosoi et al., "Memory Th1 Cells Augment Tumor-Specific CTL following Transcutaneous Peptide Immunization", Cancer Research, vol. 68, No. 10, 2008, pp. 3941-3949.
Elena Toni et al., "Bisphosphonates Target B Cells to Enhance Humoral Immune Responses", Cell Reports, vol. 5, No. 2, 2013, pp. 323-330.
Zhengrong Cui et al., "Bilayer Films for Mucosal (Genetic) Immunization via the Buccal Route in Rabbits", Pharmaceutical Research, vol. 19, No. 7, 2002, pp. 947-953.

(Continued)

*Primary Examiner* — Barry A Chestnut

(74) *Attorney, Agent, or Firm* — Greenblum & Bernstein, P.L.C.

(57) ABSTRACT

The present invention aims to provide a vaccine pharmaceutical composition universally usable for induction of humoral immunity against various antigens and exerting a high antibody production inducing effect. The present invention relates to a vaccine pharmaceutical composition for inducing humoral immunity, including: an antigen; and an immunity induction promoter that is a bisphosphonate.

14 Claims, 2 Drawing Sheets

(56) References Cited

OTHER PUBLICATIONS

International Search Report issued with respect to Application No. PCT/JP2015/074921, dated Nov. 17, 2015.
International Preliminary Report on Patentability issued with respect to Application No. PCT/JP2015/074921, dated Mar. 7, 2017.
Choy and Prausnitz, "The Rule of Five for Non-Oral Routes of Drug Delivery: Ophthalmic, Inhalation, and Transdermal" 2010, 28 Pharmacology Research 943.
Pub Chem entry for the minodronic acid.
Office Action for JP App. No. 2015-172941 dated Aug. 20, 2019 (w/ translation).

* cited by examiner

BISPHOSPHONATE-CONTAINING VACCINE PHARMACEUTICAL COMPOSITION FOR HUMORAL IMMUNITY

TECHNICAL FIELD

The present invention relates to a vaccine pharmaceutical composition for inducing humoral immunity.

BACKGROUND ART

Vaccines that are generally widely used aim to induce immunity for prevention of infectious diseases, and are used to administer pathogens (e.g., microorganisms and viruses) or a part thereof. Most of the vaccine formulations commercialized at present are injection products.

Commonly, invasive administration of a vaccine into the body is needed because microorganisms or viruses cannot enter the body through the skin due to their sizes. Injections, such as subcutaneous injection, intradermal injection, and intramuscular injection, are therefore commonly used for administration of vaccines for immunization.

Examples of adjuvants or immunostimulants practically used for immunization by injections include aluminum salts (e.g., aluminum hydroxide, aluminum phosphate, and aluminum chloride) and emulsions containing squalene (e.g., MF59 and AS03). Moreover, flagellar components, nucleic acids, cytokines, cationic polymers, polypeptides, and the like are also considered to be used as the adjuvants or immunostimulants.

Injections, however, have problems in terms of the quality of life (QOL) of the patients, such as pain, fear, needle marks and scarring thereof, and the burden of visiting the hospital in their daily life in a case where repeated administration is required. Additionally, injections further have problems that only medical practitioners can give them, that the intradermal injection which gives a high immune effect requires a proficient skill to give, that medical practitioners are exposed to a risk of infection due to needle pricking, and that medical waste which necessitate special disposition, such as injection needles, is generated. The injection is therefore not necessarily the best administration route.

The administration route of vaccines other than injections may be, for example, transdermal administration (see Patent Literature 1 and Non-Patent Literature 1), buccal administration, transnasal administration, sublingual administration (see Non-Patent Literature 2 and Patent Literatures 2 and 3), or the like.

Since a large number of Langerhans cells that are antigen presenting cells are present in the skin, transdermal administration or transmucosal administration is now considered as a means to avoid various problems in relation to injections.

Examples of the adjuvant or immunostimulants considered to be used for immunization by transdermal administration or transmucosal administration include aluminum salts (e.g., aluminum hydroxide, aluminum phosphate, and aluminum chloride) and toxins (e.g., cholera toxin and *Escherichia coli* heat-labile toxin).

The adjuvants or immunostimulants conventionally used for transdermal administration or transmucosal administration are limited, such as fragments derived from microorganisms or viruses, toxins (e.g., cholera toxin, *Escherichia coli* heat-labile toxin), and oil/fat adjuvants that enhance the effect by the extended-release of antigens. These adjuvants have a problem of a balance between the safety and the effect.

Moreover, immunostimulants effectively used in induction of humoral immunity by transdermal administration of antigens have been hardly reported. In many cases, transdermal administration fails to give a sufficient humoral immunity inducing effect in comparison with the case of using injections.

Bisphosphonates used for treatment of osteoporosis have recently been found to stimulate dendritic cells or γδT cells to activate the immune response. Bisphosphates are now expected to have a new application as immunostimulants.

However, a sufficient therapeutic effect cannot be expected from simple administration of a bisphosphonate because the proportion of γδT cells in the peripheral blood is only 1% to 5%. As a means to achieve a sufficient effect, Patent Literatures 4, 5, and 6 each teaches immuno-cell therapy in which γδT cells isolated from the patient's peripheral blood is stimulated in vitro, co-cultured with other immunocompetent cell(s), and returned to the patient's blood.

Patent Literature 7, for example, reports a case where sufficient antibody production is induced by injecting a bisphosphonate to stimulate dendritic cells or the like several days before the administration of virus antigens as a vaccine.

CITATION LIST

Patent Literature

Patent Literature 1: US 2008/0193487 A
Patent Literature 2: JP 2002-531415 T
Patent Literature 3: US 2008/0112974 A
Patent Literature 4: WO 2006/006638
Patent Literature 5: WO 2007/029689
Patent Literature 6: JP 2010-259373 A
Patent Literature 7: WO 2012/054807

Non-Patent Literature

Non-Patent Literature 1: Hosoi Akihiro et al., Cancer Research, 68, 3941-3949 (2008)
Non-Patent Literature 2: Zhengrong Cui et al., Pharmaceutical Research, Vol. 19, No. 7, 947-953 (2002)

SUMMARY OF INVENTION

Technical Problem

The present invention aims to provide a vaccine pharmaceutical composition universally usable for induction of humoral immunity against various antigens and exerting a high antibody production inducing effect.

Solution to Problem

The present inventors noted that bisphosphonates used for treatment of osteoporosis can activate immune response by stimulating dendritic cells or γδT cells.

The γδT cells secrete Th2 cytokines such as IL-4 and IL-13 and chemokines such as CXCL13 in addition to Th1 cytokines such as IFN-γ and TNF-α by antigenic stimulation to activate immune response of the entire body. However, since the proportion of the γδT cells in the peripheral blood is only 1% to 5%, simple administration of a bisphosphonate may not be able to induce sufficient immune response.

In the mucosal epithelium and dermis, a large number of γδT cells are present and provide innate immunity by promptly reacting against foreign invasion.

The present inventors focused on this point to find out that a direct administration of an immunity induction promoter that is a bisphosphonate together with antigens to a living body by administration on a body surface (e.g., transdermal administration and transmucosal administration) can stimulate dendritic cells or γδT cells to effectively induce antigen-specific humoral immunity.

Specifically, the present invention relates to a vaccine pharmaceutical composition to be used for inducing humoral immunity, containing: an antigen; and an immunity induction promoter that is a bisphosphonate.

The vaccine pharmaceutical composition of the present invention is preferably administered to a body surface.

The immunity induction promoter that is a bisphosphonate is preferably at least one selected from the group consisting of etidronate, clodronate, tiludronate, pamidronate, neridronate, alendronate, ibandronate, zoledronate, risedronate, and minodronate.

The present invention is specifically described in the following.

The vaccine pharmaceutical composition of the present invention is used for inducing humoral immunity.

The humoral immunity inducing effect may be quantitatively determined by any method, and various methods are available. For example, the humoral immunity inducing effect can be determined by an immunity induction test using an animal model for immunological evaluation and ELISA (antigen-specific IgG antibody). An exemplary sample for ELISA is blood of an animal model for immunological evaluation.

The vaccine pharmaceutical composition of the present invention contains an antigen and an immunity induction promoter that is a bisphosphonate.

Containing the antigen and the immunity induction promoter that is a bisphosphonate, the vaccine pharmaceutical composition of the present invention can effectively induce antigen-specific humoral immunity.

The antigen is preferably an antigen derived from an infectious disease.

The antigen derived from an infectious disease refers to any substance that can be a target of the immune response generated by a test organism. The antigen derived from an infectious disease may also be a substance that can be a target of the immune response (e.g., mature of immunocompetent cells, cytokine production, antibody production) upon contact with immunocompetent cells.

The antigen derived from an infectious disease is not limited, as long as it is an infectious pathogen or an antigen derived from an infectious pathogen.

The disease due to the infectious pathogen is not limited, and examples thereof include: virus diseases caused by infection with viruses such as adenovirus (e.g., human adenovirus), herpesvirus (e.g., herpes simplex virus, varicella-zoster virus, cytomegalovirus, human herpesvirus, or Kaposi sarcoma-associated herpesvirus), picornavirus (e.g., polio virus, common cold virus, or hepatitis A virus), pox virus (e.g., smallpox virus, vaccinia virus, or molluscum contagiosum virus), picornavirus (e.g., rhinovirus or enterovirus), orthomyxovirus (e.g., influenza virus), paramyxovirus (e.g., parainfluenza virus, mumps virus, measles virus, respiratory syncytial virus (RSV), or Newcastle disease virus), parvovirus (e.g., adeno associated virus), togavirus (e.g., rubella virus), coronavirus (e.g., SARS coronavirus), hepadnavirus (e.g., hepatitis B virus), flavivirus (e.g., Japanese encephalitis virus, yellow fever virus, dengue virus, West Nile fever virus, St. Louis encephalitis virus, Murray Valley encephalitis virus, hepatitis C virus, or hepatitis G virus), hepevirus (e.g., hepatitis E virus), papillomavirus (e.g., human papilloma virus), calicivirus (e.g., Norovirus), rhabdovirus (e.g., rabies virus or vesicular stomatitis virus), filovirus (e.g., Ebola hemorrhagic fever virus), arenavirus (e.g., Lassa virus or hepatitis D virus), bunyavirus (e.g., California encephalitis virus or Rift Valley fever virus), reovirus (e.g., rotavirus), or retrovirus (e.g., human immunodeficiency virus (HIV) or adult T-cell leukemia virus); bacterial diseases such as those caused by infection with a bacterium such as *Escherichia, Enterobacter, Salmonella, Staphylococcus*, dysentery *bacillus, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campyrobacter, Vibrio, Serratia, Providencia, Chromobacterium, Brucella, Yersinia, Haemophilus*, or *Bordetella*; fungous diseases such as *Chlamydia*, candidiasis, aspergillosis, histoplasmosis, and cryptococcal meningitis; malaria; *Pneumocystis carinii* pneumonia; leishmaniasis; cryptosporidiosis; toxoplasmosis; and *Trypanosoma* infection.

Examples of the immunity induction promoter that is a bisphosphonate include therapeutic agents for osteoporosis having a bisphosphonate skeleton and inhibiting bone resorption. Specific examples thereof include etidronate, clodronate, tiludronate, alendronate, ibandronate, pamidronate, neridronate, olpadronate, zoledronate, risedronate, minodronate, cimadronate, and incadronate. In terms of fewer side effects such as unfavorable stimulus to the site of administration or inflammation, preferred are etidronate, clodronate, and tiludronate which are referred to as first generation biophosphonates having no nitrogen atoms in the side chain. In terms of a high humoral immunity inducing effect, preferred are second generation biophosphonates (alendronate, ibandronate, pamidronate, neridronate, olpadronate) and third generation biophosphonates (zoledronate, risedronate, minodronate, cimadronate, incadronate) both having nitrogen atoms in the side chain. These compounds are each in a salt form.

In particular, the immunity induction promoter that is a bisphosphonate is more preferably at least one selected from the group consisting of etidronate, clodronate, tiludronate, pamidronate, neridronate, alendronate, ibandronate, zoledronate, risedronate, and minodronate.

As used herein, the term "salt" may refer to any organic or inorganic acid salt, and is preferably a pharmacologically acceptable salt.

As used herein, the term "pharmacologically acceptable salt" refers to a salt that does not have an adverse effect on the administration subject and does not eliminate the pharmacological activity of components of the vaccine pharmaceutical composition. Examples thereof include inorganic acid salts (e.g., hydrochloride, phosphate), organic acid salts (e.g., acetate, phthalate, TFA salt), metal salts such as alkali metal salts (e.g., sodium salt, potassium salt), alkaline earth metal salts (e.g., calcium salt, magnesium salt) and aluminum salt, and amine salts (e.g., triethylamine salt, benzylamine salt, diethanolamine salt, t-butylamine salt, dicyclohexylamine salt, arginine salt, dimethyl ammonium salt, ammonium salt).

The amount of the cellular immunity induction promoter that is a bisphosphonate in the vaccine pharmaceutical composition of the present invention is not limited. The lower limit is preferably 0.001 parts by weight and the upper limit is preferably 1,000 parts by weight based on 1 part by weight of the antigen. When the amount is less than 0.001 parts by weight, the humoral immunity inducing effect may be insufficient. When the amount is more than 1,000 parts by weight, a safety problem may arise. The lower limit of the amount is more preferably 0.005 parts by weight and the upper limit thereof is more preferably 500 parts by weight. The lower limit is still more preferably 0.01 parts by weight and the upper limit is still more preferably 100 parts by weight.

The vaccine pharmaceutical composition of the present invention may further contain, in addition to the immunity induction promoter that is a bisphosphonate, a second immunity induction promoter in such an amount that the effect of the present invention is not impaired.

The additional use of the second immunity induction promoter can further promote humoral immunity.

The amount of the second immunity induction promoter in the vaccine pharmaceutical composition of the present invention is not limited. The lower limit is preferably 0.002 parts by weight and the upper limit is preferably 500 parts by weight based on 1 part by weight of the antigen. When the amount is less than 0.002 parts by weight, the humoral immunity inducing effect may be insufficient. When the amount is more than 500 parts by weight, a safety problem may arise. The lower limit of the amount is more preferably 0.01 parts by weight and the upper limit thereof is more preferably 200 parts by weight. The lower limit is still more preferably 0.05 parts by weight and the upper limit is still more preferably 100 parts by weight.

The vaccine pharmaceutical composition of the present invention may optionally contain additive(s). The additive (s) are used in accordance with the main component of the base, compatibility with the antigen and the immunity induction promoter that is a bisphosphonate, and the intended administration regimen. Examples thereof include tonicity agents, antiseptic bactericides, antioxidants, solubilizers, solubilizer aids, suspending agents, fillers, pH adjusters, stabilizers, absorption promoters, release rate controlling agents, colorants, plasticizers, crosslinking agents, and adhesives. These additives may be used alone or in combination of two or more thereof.

The vaccine pharmaceutical composition of the present invention is preferably administered to the body surface. More preferred is transdermal administration or transmucosal administration. The vaccine pharmaceutical composition of the present invention may also be administered intradermally, subcutaneously, or intramuscularly. In other words, the vaccine pharmaceutical composition of the present invention may be a vaccine pharmaceutical composition for intradermal, subcutaneous, or intramuscular administration, but is preferably a vaccine pharmaceutical composition for transdermal administration or transmucosal administration. Administration of the vaccine pharmaceutical composition of the present invention to the subject transdermally or transmucosally can effectively induce antigen-specific humoral immunity. In the case of transdermal administration, the administration may be noninvasive or minimally invasive administration.

As used herein, the term "subject" refers to any animal in which administration of the vaccine pharmaceutical composition in practical use may induce an immune response. Typically, the term refers to mammals including human, mouse, rat, canine, feline, leporine, equine, bovine, ovine, porcine, caprine, simian, and chimpanzee. A particularly preferred subject is a human.

<Vaccine Pharmaceutical Composition for Transmucosal Administration>

Examples of transmucosal administration include sublingual administration, transnasal administration, buccal administration, rectal administration, and vaginal administration.

The dosage form of the vaccine pharmaceutical composition for transmucosal administration may be, for example, a semisolid formulation such as a gel (jelly), a cream, an ointment, or a plaster; a solution; a solid formulation such as a powder, a fine granule, a granule, a film, a tablet, or an orally disintegrating tablet (freeze dry type); a mucosal spray formulation such as an aerosol; or an inhalant. Categories, definitions, properties, production processes, and the like of these formulations are well known in the relevant art. For example, see the Japanese Pharmacopoeia, 16th edition. Any known material may be used for these formulations. Among the above dosage forms, preferred are a solution, a solid formulation (e.g., orally disintegrating tablet (freeze dry type), a film, or the like).

The amounts of the antigen and the immunity induction promoter that is a bisphosphonate in the vaccine pharmaceutical composition for transmucosal administration are not limited. The amount of the antigen is preferably 0.01 to 40% by weight, more preferably 0.1 to 30% by weight. The amount of the immunity induction promoter that is a bisphosphonate is preferably 0.01 to 40% by weight, more preferably 0.1 to 20% by weight.

A solvent usable for the solution may be, for example, an appropriate amount of water, ethanol, glycerin, or propylene glycol. The solution can be prepared by dispersing or dissolving ingredients (i.e., the antigen, the immunity induction promoter that is a bisphosphonate, and if necessary, the second immunity induction promoter, and the like) in any of these solvents.

Any base may be used for the gel (jelly). Examples thereof include hydrogel bases such as carboxyvinyl polymers, gel bases, fat-free ointment, polyvinylpyrrolidone, polyvinyl alcohol, sodium polyacrylate, carboxymethyl cellulose, starch, xanthane gum, karaya gum, sodium alginate, methylcellulose, hydroxypropyl cellulose, hydroxypropyl methylcellulose phthalate (HPMCP), cellulose acetate phthalate (CAP), carboxymethyl ethyl cellulose (CMEC), ethylcellulose, hydroxyethylcellulose, hydroxypropyl methylcellulose, a carboxyvinyl polymer, tragacanth, gum arabic, tara gum, tamarind seed gum, *psyllium* seed gum, agar, gellan gum, glucomannan, locust bean gum, guar gum, carrageenan, dextrin, dextran, amylose, potassium carboxymethyl cellulose, sodium carboxymethyl cellulose, calcium carboxymethyl cellulose, pullulan, chitosan, sodium carboxymethyl starch, *Plantago testa*, galactomannan, Eudragit, casein, alkyl alginate ester, gelatin, and polyethylene glycol. A fluidic gel and a formable gel can be prepared by dissolving any of these bases in a solvent and adding the above ingredients thereto. The solvent is preferably water. Glycerin, propylene glycol, or the like can also be used.

Examples of a base used for the cream include water/oil-type bases such as hydrophilic ointment and vanishing cream; and oil/water-type bases such as hydrophilic Vaseline, purified lanolin, Aquaphor, Eucerin, Neocerin, hydrous lanolin, cold cream, and hydrophilic plastibase. A cream can be prepared by stirring any of these bases in an oil/fat solvent or water at high speed using a homogenizer or the like and adding the above ingredients thereto.

Examples of a base used for the film include polyvinylpyrrolidone, polyvinyl alcohol, sodium polyacrylate, carboxymethyl cellulose, starch, xanthane gum, karaya gum, sodium alginate, methylcellulose, carboxyvinyl polymer, agar, hydroxypropyl cellulose, hydroxypropyl methylcellulose phthalate (HPMCP), cellulose acetate phthalate (CAP), carboxymethyl ethyl cellulose (CMEC), ethylcellulose, hydroxyethylcellulose, hydroxypropyl methylcellulose, carboxyvinyl polymer, tragacanth, gum arabic, locust bean gum, guar gum, carrageenan, dextrin, dextran, amylose, potassium carboxymethyl cellulose, sodium carboxymethyl cellulose, calcium carboxymethyl cellulose, pullulan, chitosan, sodium carboxymethyl starch, *Plantago testa*, galactomannan, aminoalkyl methacrylate copolymer E, aminoalkyl methacrylate copolymer RS, methacrylic acid copolymer L, methacrylic acid copolymer LD, methacrylic acid copolymer S, methyl acrylate-methacrylic acid-methyl methacrylate copolymer, ethyl acrylate-methyl methacrylate copolymer, polyvinyl acetal diethyl aminoacetate, casein, and alkyl alginate ester. A film can be prepared by dissolving any of these bases in water or an organic polar solvent such as ethanol, adding the above ingredients thereto, and applying the resulting material to form a thin film, followed by drying.

The additives used for the powder, fine granule, granule, tablet, and the like are not limited. Examples thereof include excipients such as lactose, corn starch, and crystalline cellulose, and bonding agents such as hydroxypropyl cellulose and gum arabic. The powder, fine granule, granule, tablet, or the like can be prepared by adding these additives to an appropriate amount of water or a solvent such as ethanol, adding the above ingredients thereto, mixing and stirring the mixture, and performing a combination of processes such as granulation, drying, and tableting. If needed, a lubricant such as magnesium stearate or a coating agent such as hydroxypropyl cellulose or sucrose can also be added.

Examples of the base usable for the orally disintegrating tablet (freeze dry type) include polysaccharides such as gelatin and pullulan and hydrogel bases such as hydroxypropyl cellulose. In addition, mannitol, trehalose, sorbitol, glycine, or the like may be used as a forming aid. The orally disintegrating tablet (freeze dry type) can be prepared by dissolving any of these bases and forming aids in water, adding the above ingredients, dispensing and freeze drying the resulting material.

The aerosol may contain, for example, a solution, a gel having high fluidity, a cream, or fine powder such as a powdered drug. Dispersing the content as solid or liquid microparticles in a gas using a spray device enables effective administration to an administration site such as the oral mucosa or the nasal mucosa.

<Vaccine Pharmaceutical Composition for Transdermal Administration>

The dosage form of the vaccine pharmaceutical composition for transdermal administration may be a solution for external application such as a liniment or a lotion; a spray for external application such as an aerosol; a gel; a patch such as a tape, or a poultice; an ointment, a plaster, or a cream. Categories, definitions, properties, production processes, and the like of these formulations are well known in the relevant art. For example, see the Japanese Pharmacopoeia, 16th Edition. Any known material may be used for these formulations. Among the above dosage forms, preferred are a cream and a patch (tape, poultice).

The amounts of the antigen and the immunity induction promoter that is a bisphosphonate in the vaccine pharmaceutical composition for transdermal administration (in the case of a tape, in an adhesive layer) are not limited. The amount of the antigen is preferably 0.01 to 40% by weight, more preferably 0.1 to 30% by weight. The amount of the immunity induction promoter that is a bisphosphonate is preferably 0.01 to 40% by weight, more preferably 0.1 to 20% by weight.

Examples of a base used for the liniment include water, ethanol, fatty oils, hard paraffin, soft paraffin, liquid paraffin, glycerin, paraffin oil, beeswax, metal soap, mucilage, natural oils (such as almond oil, corn oil, peanut oil, castor oil, olive oil, and derivatives thereof (e.g., polyoxyl castor oil)), mutton tallow or derivatives thereof, and fatty acids and/or esters (e.g., stearic acid, oleic acid, and isopropyl myristate).

The lotion is a formulation containing ingredients finely and homogeneously dispersed in an aqueous solution, and may be a suspension-type lotion or an emulsion-type lotion. Examples of the suspending agent include gum arabic, sodium alginate, sodium carboxymethyl cellulose, methylcellulose, and bentonite. Examples of the emulsifier include sodium lauryl sulfate and sorbitan fatty acid esters.

Examples of a base usable for the ointment include those commonly used as hydrophobic bases such as oils/fats, waxes, or hydrocarbon compounds. Specific examples of the base for the ointment include mineral bases such as yellow Vaseline, white Vaseline, paraffin, liquid paraffin, plastibase, and silicone, and animal or plant bases such as beeswax and animal or plant fats and/or oils.

Examples of a base usable for the cream include water/oil-type bases such as hydrophilic ointment and vanishing cream; and oil/water-type bases such as hydrophilic Vaseline, purified lanolin, Aquaphor, Eucerin, Neocerin, hydrous lanolin, cold cream, and hydrophilic plastibase.

Any base may be used for the gel. Examples thereof include hydrogel base such as carboxyvinyl polymers, gel bases, fat-free ointment, polyvinylpyrrolidone, polyvinyl alcohol, sodium polyacrylate, carboxymethyl cellulose, starch, xanthane gum, karaya gum, sodium alginate, methylcellulose, hydroxypropyl cellulose, hydroxypropyl methylcellulose phthalate (HPMCP), cellulose acetate phthalate (CAP), carboxymethyl ethyl cellulose (CMEC), ethylcellulose, hydroxyethylcellulose, hydroxypropyl methylcellulose, carboxyvinyl polymer, tragacanth, gum arabic, tara gum, tamarind seed gum, *psyllium* seed gum, agar, gellan gum, glucomannan, locust bean gum, guar gum, carrageenan, dextrin, dextran, amylose, potassium carboxymethyl cellulose, sodium carboxymethyl cellulose, calcium carboxymethyl cellulose, pullulan, chitosan, sodium carboxymethyl starch, *Plantago testa*, galactomannan, aminoalkyl methacrylate copolymer E, aminoalkyl methacrylate copolymer RS, methacrylic acid copolymer L, methacrylic acid copolymer LD, methacrylic acid copolymer S, methyl acrylate-methacrylic acid-methyl methacrylate copolymer, ethyl acrylate-methyl methacrylate copolymer, polyvinyl acetal diethyl aminoacetate, casein, alkyl alginate ester, gelatin, and polyethylene glycol.

Any base may be used for the poultice. Examples thereof include gelatin, sodium carboxymethyl cellulose, methylcellulose, sodium polyacrylate, kaolin, polyvinyl alcohol, polyvinylpyrrolidone, glycerin, propylene glycol, and water.

The tape preferably includes an adhesive layer containing ingredients (i.e., the antigen, the immunity induction promoter that is a bisphosphonate, and if necessary, the second immunity induction promoter), and a support that supports the adhesive layer. The tape may further include a release liner that prevents exposure of the adhesive layer before use and that can be easily removed from the adhesive layer at the time of use.

Any adhesive may be used to form the adhesive layer. Examples of adhesives include acrylic adhesives containing acrylic polymers; rubber adhesives containing rubber elastomer; silicone adhesives such as silicone rubber, dimethylsiloxane-based adhesives, and diphenylsiloxane-based adhesives; vinyl ether adhesives such as polyvinyl methyl ether, polyvinyl ethyl ether, and polyvinyl isobutyl ether; vinyl ester adhesives such as vinyl acetate-ethylene copolymer; and polyester adhesives containing a carboxylic acid component (e.g., dimethyl terephthalate, dimethyl isophthalate, dimethyl phthalate), and a polyhydric alcohol component (e.g., ethylene glycol). Particularly preferred adhesives are acrylic adhesives, rubber adhesives, and silicone adhesives. Preferred is a hydrophilic base such as sodium polyacrylate because diffusional release of the antigen is favorable.

The amount of the adhesive in the adhesive layer is not limited, and is preferably 10 to 90% by weight, more preferably 20 to 80% by weight in terms of solids based on the total weight of the adhesive layer.

The acrylic adhesive preferably contains, as a main component, a polymer that contains alkyl (meth)acrylate as a first monomer.

Examples of the first monomer include alkyl (meth) acrylates having a C1-C18 linear, branched, or cyclic alkyl group. In particular, preferred are alkyl (meth)acrylates having a C4-C18 linear, branched, or cyclic alkyl group. Further, since a monomer component that lowers the glass transition temperature of a polymer is suitably used to impart adhesiveness at room temperature, an alkyl (meth) acrylate having a C4-C8 linear, branched, or cyclic alkyl group (e.g., butyl, pentyl, hexyl, cyclohexyl, heptyl, octyl, 2-ethylhexyl; preferably butyl, 2-ethylhexyl, or cyclohexyl; particularly preferably 2-ethylhexyl) is more preferred.

Specifically, the first monomer is preferably butyl acrylate, 2-ethylhexyl acrylate, 2-ethylhexyl methacrylate, cyclohexyl acrylate, or cyclohexyl methacrylate, particularly preferably 2-ethylhexyl acrylate. These first monomers may be used alone or in combination of two or more thereof.

The first monomer may be copolymerized with a second monomer. Such a second monomer may be a monomer having a functional group that can form a crosslinking point when a crosslinking agent is used. Examples of functional groups capable of being involved in crosslinking reactions include groups such as hydroxy, carboxy, and vinyl groups. Among these, hydroxy and carboxy groups are preferred.

Specific examples of the second monomer include hydroxyethyl (meth)acrylate, hydroxypropyl (meth)acrylate, N-hydroxyalkyl (meth)acrylamide, (meth)acrylic acid, itaconic acid, maleic acid, maleic anhydride, mesaconic acid, citraconic acid, and glutaconic acid. Among these, acrylic acid, methacrylic acid, hydroxyethyl acrylate (particularly, 2-hydroxyethyl acrylate) are preferred, and acrylic acid is the most preferred, in view of easy availability. These second monomers may be used alone or in combination of two or more thereof.

Moreover, the first monomer and second monomer may be further copolymerized with a third monomer.

Examples of the third monomer include vinyl esters such as vinyl acetate and vinyl propionate; vinyl ethers such as methyl vinyl ether and ethyl vinyl ether; vinyl amides such as N-vinyl-2-pyrrolidone and N-vinylcaprolactam; alkoxy (meth)acrylates such as methoxyethyl (meth)acrylate, ethoxyethyl (meth)acrylate, and tetrahydrofurfuryl (meth) acrylate; hydroxy group-containing monomers (as the third monomer, not as a crosslinking point) such as hydroxypropyl(meth)acrylate and α-hydroxymethyl acrylate; (meth) acrylic acid derivatives having an amide group such as (meth)acrylamide, dimethyl (meth)acrylamide, N-butyl (meth)acrylamide, and N-methylol (meth)acrylamide; aminoalkyl (meth)acrylates such as aminoethyl (meth)acrylate, dimethylaminoethyl (meth)acrylate, and t-butyl aminoethyl (meth)acrylate; alkoxyalkylene glycol (meth)acrylates such as methoxyethylene glycol (meth)acrylate, methoxydiethylene glycol (meth)acrylate, methoxypolyethylene glycol (meth)acrylate, and methoxypolypropylene glycol (meth)acrylate; (meth)acrylonitrile; monomers containing sulfonic acid such as styrenesulfonic acid, allylsulfonic acid, sulfopropyl(meth)acrylate, (meth)acryloyloxy naphthalene sulfonate, and acrylamide methylsulfonate; and vinyl group-containing monomers such as vinylpiperidone, vinylpyrimidine, vinylpiperazine, vinylpyrrole, vinylimidazole, vinyloxazole, and vinylmorpholine. Preferred among these are vinyl esters and vinyl amides. Vinyl acetate is preferred among vinyl esters, and N-vinyl-2-pyrrolidone is preferred among vinyl amides. These third monomers may be used alone or in combination of two or more thereof.

In the case of a copolymer of the alkyl (meth)acrylate (first monomer) and the vinyl monomer having a functional group capable of being involved in crosslinking reaction (second monomer), the alkyl (meth)acrylate and the vinyl monomer having a functional group capable of being involved in crosslinking reaction are preferably copolymerized at a weight ratio of (99-85):(1-15), more preferably at a weight ratio of (99-90):(1-10).

In the case of a copolymer of the alkyl (meth)acrylate (first monomer), the vinyl monomer having a functional group that can be involved in a crosslinking reaction (second monomer), and a different monomer other than these (third monomer), the alkyl (meth)acrylate, the vinyl monomer having a functional group capable of being involved in crosslinking reaction, and the different monomer are preferably copolymerized at a weight ratio of (40-94):(1-15):(5-50), more preferably at a weight ratio of (50-89):(1-10):(10-40).

The polymerization reaction may be carried out by any conventionally known method. For example, the above monomers may be reacted in the presence of an initiator (e.g., benzoyl peroxide or azobisisobutyronitrile) in a solvent (e.g., ethyl acetate) at 50° C. to 70° C. for 5 to 48 hours.

The acrylic adhesive preferably contains a 2-ethylhexyl acrylate/acrylic acid/N-vinyl-2-pyrrolidone copolymer, a 2-ethylhexyl acrylate/N-(2-hydroxyethyl)acrylamide/N-vinyl-2-pyrrolidone copolymer, a 2-ethylhexyl acrylate/2-hydroxyethyl acrylate/vinyl acetate copolymer, or a 2-ethylhexyl acrylate/acrylic acid copolymer, more preferably contains a 2-ethylhexyl acrylate/acrylic acid/N-vinyl-2-pyrrolidone copolymer.

The acrylic adhesive may be subjected to physical crosslinking treatment by radiation such as ultraviolet irradiation or electron beam irradiation, or chemical crosslinking treatment using various crosslinking agents such as an isocyanate compound (e.g., trifunctional isocyanate), an organic peroxide, an organic metal salt, a metal alcoholate, a metal chelate compound, or a polyfunctional compound (e.g., a polyfunctional external crosslinking agent, a polyfunctional monomer for internal crosslinking such as di(meth)acrylate).

Examples of the rubber elastomer used for the rubber adhesive include polyisobutylene/polybutene elastomer, a styrene/diene/styrene block copolymer, styrene/butadiene elastomer, nitrile elastomer, chloroprene elastomer, vinylpyridine elastomer, polyisobutylene elastomer, butyl elastomer, and isoprene-isobutylene elastomer. Preferred among these are polyisobutylene (PIB) and a styrene/diene/styrene block copolymer (such as a styrene/butadiene/styrene block copolymer (SBS) or a styrene/isoprene/styrene block copolymer (SIS)), in view of solubility to the ingredients and the skin adhesiveness. These rubber elastomers may be used alone or in combination of two or more thereof.

In order to achieve appropriate adhesion and solubility to the ingredients, the rubber adhesive may be a mixture of rubber elastomers formed from the same or different components and different in the average molecular weight. For example, a mixture of a high-molecular-weight polyisobutylene having an average molecular weight of 150,000 to 5,500,000 and a medium-molecular-weight polyisobutylene having an average molecular weight of 10,000 to 150,000 and/or a low-molecular-weight polyisobutylene having an average molecular weight of 500 to 4,000 is preferred. The weight ratio of the high-molecular-weight polyisobutylene to the middle-molecular-weight polyisobutylene and/or the low-molecular-weight polyisobutylene is preferably (10 to 80 (more preferably 20 to 70)):(0 to 90 (more preferably 0 to 80, still more preferably 10 to 60)).

As user herein, the term "average molecular weight" refers to a viscosity average molecular weight calculated from the Flory viscosity equation. The average molecular weight is determined by calculating the Staudinger index ($J_0$) from the flow time at 20° C. of the capillary 1 of an Ubbelohde viscometer by the Schulz-Blaschke equation, and using this $J_0$ value in the following expression.

$$J_0 = n_{sp}/c(1+0.31 n_{sp})$$

$$n_{sp} = t/t_0 - 1 \quad \text{(Schulz-Blaschke equation)}$$

t: Flow time of solution (according to Hagenbach-couette correction formula)
$t_0$: Flow time of solvent (according to Hagenbach-couette correction formula)
c: Concentration of solution (g/cm$^3$)

$$J_0 = 3.06 \times 10^{-2} \overline{Mv}^{0.65}$$

$\overline{Mv}$: Viscosity average molecular weight

In order to provide appropriate tackiness, the rubber adhesive may contain a tackifier such as rosin resin, polyterpene resin, coumarone-indene resin, petroleum resin, terpene-phenol resin, xylene resin, or alicyclic saturated hydrocarbon resin. These tackifiers may be used alone or in combination of two or more thereof.

The amount of the tackifier is preferably 50% by weight or less, more preferably 5 to 40% by weight based on the total weight of the rubber adhesive.

Examples of the silicone adhesive include polyorganosiloxane adhesives, polydimethylsiloxane adhesives, and polydimethyldiphenyl-siloxane adhesives. In particular, commercially available silicone adhesives such as BIO PSA (Dow Corning Corporation) are preferred.

The adhesive layer may further contain a skin permeation enhancer.

As used herein, the term "skin permeation enhancer" refers to any substance that may improve the efficiency of skin permeation of a transdermally administered antigen.

The skin permeation enhancer is preferably liquid (i.e., having fluidity) at room temperature (25° C.). In the case where two or more kinds of skin permeation enhancers are mixed, the final mixture is preferably liquid at room temperature (25° C.) and has an effect of enhancing skin permeation. Such an organic liquid component is preferably a hydrophobic liquid component in terms of the compatibility in the adhesive.

Examples of the skin permeation enhancer include higher alcohols, fatty acid esters, and polyhydric alcohol fatty acid esters.

The higher alcohol is preferably a C8-C18 higher alcohol, more preferably a C8-C14 higher alcohol. The fatty acid ester is preferably a fatty acid ester of a C8-C18 fatty acid and a C1-C18 monohydric alcohol, more preferably a fatty acid ester of a C12-C16 fatty acid and a C1-C18 monohydric alcohol. In particular, preferred are fatty acid esters, and particularly preferred are isopropyl myristate, isopropyl palmitate, and diethyl sebacate.

Specific examples of the skin permeation enhancer include higher alcohols such as oleyl alcohol and octyldodecanol; polyhydric alcohols such as glycerin, ethylene glycol, and polypropylene glycol; higher fatty acids such as oleic acid and caprylic acid; fatty acid esters such as isopropyl myristate, isopropyl palmitate, and ethyl oleate; polybasic acid esters such as diethyl sebacate and diisopropyl adipate; polyhydric alcohol fatty acid esters such as diglyceryl triisostearate, sorbitan monooleate, propylene glycol dicaprylate, polyethylene glycol monolaurate, and polyoxyethylene sorbitol tetraoleate; polyoxyethylene alkyl ethers such as polyoxyethylene lauryl ether; hydrocarbons such as squalane or liquid paraffin; vegetable oils such as olive oil and castor oil; silicone oil; pyrrolidones such as N-methylpyrrolidone and N-dodecyl pyrrolidone; and sulfoxides such as decyl methyl sulfoxide. These skin permeation enhancers may be used alone or in combination of two or more thereof.

In the case of using the acrylic adhesive or rubber adhesive, the skin permeation enhancer used may be, for example, polyvinyl pyrrolidone, crospovidone, polypropylene glycol, polyvinyl alcohol, carboxy vinyl polymer, hydroxypropyl cellulose, or a mixture of these. Preferred among these are polyvinyl pyrrolidone, crospovidone, and polypropylene glycol.

The amount of the skin permeation enhancer in the adhesive layer is not limited, and is preferably 0.1 to 70% by weight, more preferably 1 to 65% by weight, still more preferably 5 to 60% by weight, based on the total weight of the adhesive layer. When the amount of the skin permeation enhancer is 0.1% by weight or more, the effect of promoting skin permeation is high. When the amount of the skin permeation enhancer is 70% by weight or less, the effect of promoting skin permeation is high, while reduction in the adhesion and the cohesion of the entire adhesive layer is suppressed.

The adhesive layer may have any thickness. Preferably, the thickness is 10 to 1,000 μm. With the thickness within the above range, the adhesive layer can readily contain the ingredients each in an effective amount and exhibit sufficient adhesion. Moreover, the adhesive layer with such a thickness can be readily formed.

The support is not limited, and is preferably one substantially impermeable to the above ingredients. In other words, it is preferably one that prevents a decrease in the amount of the antigen, the immunity induction promoter that is a bisphosphonate, and optionally the second immunity induction promoter contained in the adhesive layer by not allowing them to pass through the support and escape from the back side.

The support may be a single film of polyester, polyamide, polyvinylidene chloride, polyethylene, polypropylene, polyvinyl chloride, ethylene-ethyl acrylate copolymer, polytetrafluoroethylene, ionomer resin, metal foil, or the like, or it may be a laminated film of these mentioned above. Preferred among these is a laminated film of a nonporous plastic film which is made of any of the above-mentioned materials and a porous film, in view of achieving good adhesiveness (anchoring properties) between the support and the adhesive layer. In this case, the adhesive layer is preferably formed on the porous film side.

Any porous film that improves the anchoring properties between the support and the adhesive layer may be used. Examples thereof include paper, woven fabrics, nonwoven fabrics, knitted fabrics, and mechanically perforated sheets. Preferred among these are paper, woven fabrics, and nonwoven fabrics, in view of factors such as handleability. A porous film having a thickness in the range of 1 to 200 μm is preferably employed in view of improving anchoring properties and also in view of factors such as flexibility and attachment operability of the tape. In addition, in the case where the porous film is a woven fabric or a nonwoven fabric, the weight per unit area is preferably 5 to 30 g/m$^2$, more preferably 6 to 15 g/m$^2$.

The most suitable support is a laminated film of a polyester film (preferably, a polyethylene terephthalate film) having a thickness of 1.5 to 6 μm and a polyester (preferably, polyethylene terephthalate) nonwoven fabric having a weight per unit area of 6 to 15 g/m$^2$.

The release liner is not limited as long as it is preliminarily subjected to release treatment and ensures sufficiently light releasability. Examples thereof include films made of polyester, polyvinyl chloride, polyvinylidene chloride, polyethylene terephthalate, or the like; paper such as wood-free paper and glassine paper; and laminate films of wood-free paper or glassine paper and polyolefin, which are preliminarily treated to be releasable by applying, for example, silicone resin or fluorine resin to the surface to be in contact with the adhesive layer.

The thickness of the release liner is preferably 10 to 200 μm, more preferably 25 to 100 μm.

The release liner is preferably formed from polyester (in particular, polyethylene terephthalate) resin in view of factors such as barrier and cost. In this case, the thickness of the release liner is preferably about 25 to 100 μm in view of handleability.

<Vaccine Pharmaceutical Composition for Intradermal, Subcutaneous, or Intramuscular Administration>

The dosage form of the vaccine pharmaceutical composition for intradermal, subcutaneous, or intramuscular administration is an injectable form with a certain level of fluidity, and may be, for example a solution, a water-soluble or hydrophobic suspension, or a cream. Categories, definitions, properties, production processes, and the like of these formulations are well known in the relevant art. For example, see the Japanese Pharmacopoeia, 16th Edition. Any known material may be used for these formulations.

The amounts of the antigen and the immunity induction promoter that is a bisphosphonate in the vaccine pharmaceutical composition for intradermal, subcutaneous, or intramuscular administration are not limited. The amount of the antigen is preferably 0.01 to 40% by weight, more preferably 0.1 to 30% by weight. The amount of the immunity induction promoter that is a bisphosphonate is preferably 0.001 to 30% by weight, more preferably 0.01 to 20% by weight.

A solvent usable for the solution may be an appropriate amount of water, saline, ethanol, glycerin, propylene glycol, or the like. The solution can be prepared by dispersing or dissolving the above ingredients in any of these solvents.

Any base may be used for the water-soluble suspension, and examples thereof include a hydrogel base such as carboxy vinyl polymers, gel bases, fat-free ointments, polyvinylpyrrolidone, polyvinyl alcohol, sodium polyacrylate, carboxymethyl cellulose, starch, xanthan gum, karaya gum, sodium alginate, methylcellulose, hydroxypropyl cellulose, hydroxypropyl methylcellulose phthalate (HPMCP), cellulose acetate phthalate (CAP), carboxymethyl ethyl cellulose (CMEC), ethylcellulose, hydroxyethylcellulose, hydroxypropyl methylcellulose, carboxyvinyl polymer, tragacanth, gum arabic, tara gum, tamarind seed gum, *psyllium* seed gum, agar, gellan gum, glucomannan, locust bean gum, guar gum, carrageenan, dextrin, dextran, amylose, potassium carboxymethyl cellulose, sodium carboxymethyl cellulose, calcium carboxymethyl cellulose, pullulan, chitosan, sodium carboxymethyl starch, *Plantago testa*, galactomannan, Eudragit, casein, alkyl alginate, gelatin, or polyethylene glycol. A fluidic suspension can be prepared by dissolving any of these bases in a solvent and adding the above ingredients. The solvent is preferably saline, and may also be glycerin, propylene glycol, or the like.

Examples of the base usable for the hydrophobic suspension include water/oil-type bases such as hydrophilic ointment and vanishing cream; and oil/water-type bases such as hydrophilic Vaseline, purified lanolin, Aquaphor, Eucerin, Neocerin, hydrous lanolin, cold cream, and hydrophilic plastibase. The oil/fat suspension can be prepared by stirring any of these bases in an oil/fat solvent or water with a homogenizer at high speed and adding the above ingredients.

In administration of the vaccine pharmaceutical composition of the present invention to the subject, the therapeutically effective amount of the antigen may widely vary depending on the severity of the disease, age and relative health of the subject, and other known factors. Generally, satisfactory results can be obtained at a dose of about 0.1 μg to 1 g/kg body weight per day. The immunity induction promoter that is a bisphosphonate is simultaneously or sequentially administered with the antigen. Simultaneous administration is preferred.

The therapeutically effective amount of the immunity induction promoter that is a bisphosphonate may widely vary depending on the specific type of the bisphosphonate used and the presence or absence of other immunity induction promoter(s). Generally, satisfactory results can be obtained at about 0.01 μg to 1 g/kg body weight per day.

The daily dose may be administered in one time, or may be split into multiple doses (i.e., two or more doses, for example, 2, 3, 4, or 5 doses). Preferably, the period of continuous administration per dose is appropriately determined in the range from 1 minute to 7 days. Preferably, the administration interval is appropriately selected from once a day to once a year (for example, once a day, once every 2 days, once every 3 days, once a week, once every 2 weeks, once a month, once every 3 months, once every 6 months, once a year, etc.), or longer administration intervals, depending on the condition of patients, severity of the disease, and whether it is for therapeutic purposes or preventive purposes. Generally, for the therapeutic purposes for a patient actually having a severe disease, the vaccine pharmaceutical composition of the present invention is preferably administered at a higher frequency and/or in a higher dose, while for the preventive purposes for patients not having a disease, the vaccine pharmaceutical composition of the present invention is preferably administered at a lower frequency and/or in a lower dose.

Advantageous Effects of Invention

Since allowing the noninvasive administration to the body surface (e.g., transdermal administration or transmucosal administration), the vaccine pharmaceutical composition of the present invention can provide the following advantages. Specifically, excellent compliance owing to noninvasive administration (e.g., transdermal administration or transmucosal administration) or minimally invasive administration (e.g., administration to the skin surface after corneum exfoliation such as tape stripping, or corneum perforation such as micro needling or electroporation) is achieved; patients are free from pain or fear of injections; patients can perform administration by themselves as the administration is easy; medical practitioners can avoid a risk of infection due to needle pricking; in a case where repetitive administration is needed, the ambulatory frequency can be reduced to contribute to the improvement in quality of life of the patient; and medical wastes (e.g., needles) which necessitate special disposition are not generated.

In the case of the vaccine pharmaceutical composition of the present invention in the form of a patch such as a tape or a poultice, it is advantageous in that a predetermined dose can be reliably administered; the drug release rate can be controlled at any rate; and the drug is prevented from being attached to a site other than the intended site. In addition, since a patch is easily detachable, it is advantageous in that patients can immediately discontinue administration on their own by removing the patch from the site of application when an adverse effect occurs, for example.

Administration of the vaccine pharmaceutical composition of the present invention gives a significantly improved antibody production inducing effect compared to administration of the antigen alone. The use of the vaccine pharmaceutical composition of the present invention for noninvasive administration to the body surface (e.g., transdermal administration or transmucosal administration) can induce stronger immunity compared to administration by injections.

DESCRIPTION OF EMBODIMENTS

Figure 1:
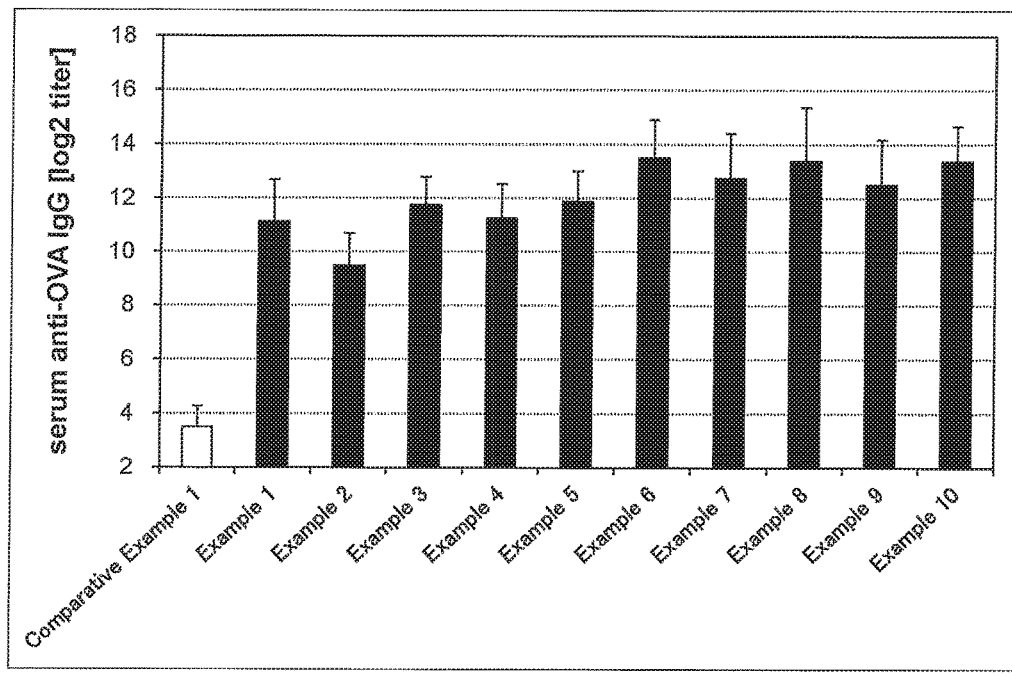
FIG. 1 is a graph showing antigen (OVA)-specific IgG titers in mouse serums after transnasal administration of solutions for transmucosal administration obtained in examples and comparative examples.

The present invention is described specifically in detail in the following with reference to, but not limited to, examples.

Examples 1 to 20, Comparative Examples 1 and 2

(Preparation of Solution for Transmucosal Administration)

Solutions for transmucosal administration (transnasal administration or sublingual administration) having a composition shown in Table 1 and 2 were prepared. Specifically, an antigen (ovalbumin (OVA), Sigma-Aldrich Co. LLC) and an immunity induction promoter that is a bisphosphonate each in an amount as shown in Table 1 or 2 were blended, followed by addition of saline thereto. The mixture was mixed to give a solution for transmucosal administration (transnasal administration or sublingual administration).

As the immunity induction promoter that is a bisphosphonate, etidronate (LKT Laboratories, Inc.), clodronate (LKT Laboratories, Inc.), tiludronate (Sigma-Aldrich Co. LLC), pamidronate (Sigma-Aldrich Co. LLC), neridronate (Sigma-Aldrich Co. LLC), alendronate (medichem), ibandronate (URQUIMA S.A.), zoledronate (Konan Chemical Industry co., ltd.), risedronate (Propharma S.A.), or minodronate (Ava Chem Scientific) was used.

TABLE 1

| | | | Composition [μg] | | | | | | | | | | | |
|---|---|---|---|---|---|---|---|---|---|---|---|---|---|---|
| | | | Example | | | | | | | | | | | Comparative Example |
| Component | | | 1 | 2 | 3 | 4 | 5 | 6 | 7 | 8 | 9 | 10 | 1 |
| Antigen | OVA | | 1 | 1 | 1 | 1 | 1 | 1 | 1 | 1 | 1 | 1 | 1 |
| Immunity induction promoter | Bisphosphonate | Etidronate | 10 | — | — | — | — | — | — | — | — | — | — |
| | | Clodronate | — | 10 | — | — | — | — | — | — | — | — | — |
| | | Tiludronate | — | — | 10 | — | — | — | — | — | — | — | — |
| | | Pamidronate | — | — | — | 10 | — | — | — | — | — | — | — |
| | | Neridronate | — | — | — | — | 10 | — | — | — | — | — | — |
| | | Alendronate | — | — | — | — | — | 10 | — | — | — | — | — |
| | | Ibandronate | — | — | — | — | — | — | 10 | — | — | — | — |
| | | Zoledronate | — | — | — | — | — | — | — | 10 | — | — | — |
| | | Risedronate | — | — | — | — | — | — | — | — | 10 | — | — |
| | | Minodronate | — | — | — | — | — | — | — | — | — | 10 | — |
| Saline [μL] | | | 10.0 | 10.0 | 10.0 | 10.0 | 10.0 | 10.0 | 10.0 | 10.0 | 10.0 | 10.0 | 10.0 |
| Dosage form | | | Solution | | | | | | | | | | |
| Administration route | | | Transnasal administration | | | | | | | | | | |

TABLE 2

| | | | Composition [μg] | | | | | | | | | | |
|---|---|---|---|---|---|---|---|---|---|---|---|---|---|
| | | | Example | | | | | | | | | | Comparative Example |
| Component | | | 11 | 12 | 13 | 14 | 15 | 16 | 17 | 18 | 19 | 20 | 2 |
| Antigen | OVA | | 1 | 1 | 1 | 1 | 1 | 1 | 1 | 1 | 1 | 1 | 1 |
| Immunity induction promoter | Bisphosphonate | Etidronate | 100 | — | — | — | — | — | — | — | — | — | — |
| | | Clodronate | — | 100 | — | — | — | — | — | — | — | — | — |
| | | Tiludronate | — | — | 100 | — | — | — | — | — | — | — | — |
| | | Pamidronate | — | — | — | 100 | — | — | — | — | — | — | — |
| | | Neridronate | — | — | — | — | 100 | — | — | — | — | — | — |
| | | Alendronate | — | — | — | — | — | 100 | — | — | — | — | — |
| | | Ibandronate | — | — | — | — | — | — | 100 | — | — | — | — |
| | | Zoledronate | — | — | — | — | — | — | — | 50 | — | — | — |
| | | Risedronate | — | — | — | — | — | — | — | — | 50 | — | — |
| | | Minodronate | — | — | — | — | — | — | — | — | — | 50 | — |
| Saline [μL] | | | 30.0 | 30.0 | 30.0 | 30.0 | 30.0 | 30.0 | 30.0 | 30.0 | 30.0 | 30.0 | 30.0 |
| Dosage form | | | Solution | | | | | | | | | | |
| Administration route | | | Sublingual administration | | | | | | | | | | |

Examples 21 to 32, Comparative Examples 3 and 4

(Preparation of Solid Formulation for Sublingual Administration)

Solid formulations (freeze dry formulations or films) for sublingual administration having a composition as shown in Table 3 were prepared. Specifically, an antigen (ovalbumin (OVA), Sigma-Aldrich Co. LLC), an immunity induction promoter that is a bisphosphonate, and hydroxypropyl cellulose (HPC-SSL, Nippon Soda Co., Ltd.) as a base each in an amount as shown in Table 3 were blended, followed by addition of saline thereto. The mixture was mixed to give a drug solution. The drug solution was divided into 25-mg portions, and then freeze-dried to give a freeze dry formulation or dried under reduced pressure to give a film. The immunity induction promoter that is a bisphosphonate used was the same as that used for preparation of a solution for transmucosal administration.

(Evaluation of the Humoral Immunity Inducing Effect)

Figure 2:
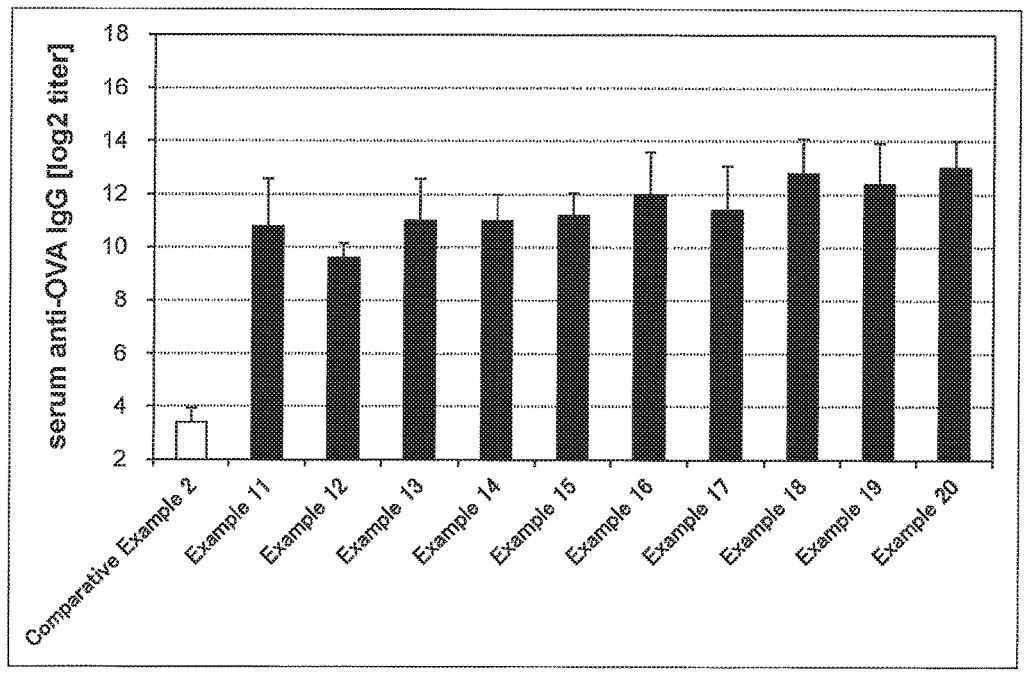
FIG. 2 is a graph showing antigen (OVA)-specific IgG titers in mouse serums after sublingual administration of solutions for transmucosal administration obtained in examples and comparative examples.
Figure 3:
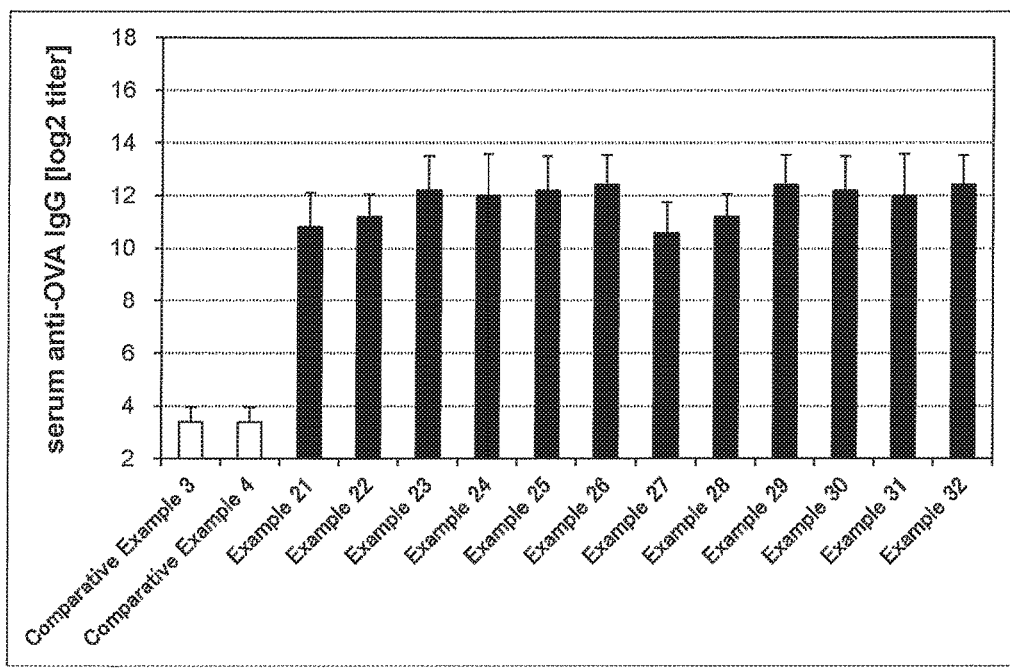
FIG. 3 is a graph showing antigen (OVA)-specific IgG titers in mouse serums after sublingual administration of solid formulations for sublingual administration obtained in examples and comparative examples.

In accordance with the following procedure, a mouse immunity test using an animal model for immunological evaluation was performed with the solution for transmucosal administration or the solid formulation for sublingual administration. Then, the antigen (OVA)-specific IgG antibody in the mouse serum was analyzed for evaluation of the systemic immune response. FIGS. 1 to 3 show the evaluation results.

(1) Mouse Immunity Test of Solution for Transmucosal Administration or Solid Formulation for Sublingual Administration A mouse (BALB/c mice, female, 7 weeks old) prepared was anesthetized. The solution for transmucosal administration was administered to the mouse by transnasal administration (10 μL, Examples 1 to 10, Comparative Example 1 (Table 1)) or sublingual administration (30 μL, Examples 11 to 20, Comparative Example 2 (Table 2)). Similarly, the

TABLE 3

| | | | Composition [parts by weight] | | | | | | | | | | | | | |
|---|---|---|---|---|---|---|---|---|---|---|---|---|---|---|---|---|
| | | | Example | | | | | | | | | | | | Comparative Example | |
| Component | | | 21 | 22 | 23 | 24 | 25 | 26 | 27 | 28 | 29 | 30 | 31 | 32 | 3 | 4 |
| Antigen | OVA | | 0.1 | 0.1 | 0.1 | 0.1 | 0.1 | 0.1 | 0.1 | 0.1 | 0.1 | 0.1 | 0.1 | 0.1 | 0.1 | 0.1 |
| Immunity induction promoter | Bisphosphonate | Etidronate | 10 | — | — | — | — | — | 10 | — | — | — | — | — | — | — |
| | | Pamidronate | — | 10 | — | — | — | — | — | 10 | — | — | — | — | — | — |
| | | Alendronate | — | — | 10 | — | — | — | — | — | 10 | — | — | — | — | — |
| | | Zoledronate | — | — | — | 5 | — | — | — | — | — | 5 | — | — | — | — |
| | | Risedronate | — | — | — | — | 5 | — | — | — | — | — | 5 | — | — | — |
| | | Minodronate | — | — | — | — | — | 5 | — | — | — | — | — | 5 | — | — |
| Base | HPO-SSL | | 250 | 250 | 250 | 250 | 250 | 250 | 250 | 250 | 250 | 250 | 250 | 250 | 250 | 250 |
| Saline | | | 739.9 | 739.9 | 739.9 | 744.9 | 744.9 | 744.9 | 739.9 | 739.9 | 739.9 | 744.9 | 744.9 | 744.9 | 749.9 | 749.9 |
| Dispensing amount [mg/mouse] | | | 25.0 | 25.0 | 25.0 | 25.0 | 25.0 | 25.0 | 25.0 | 25.0 | 25.0 | 25.0 | 25.0 | 25.0 | 25.0 | 25.0 |
| Dosage form | | | Solid (freeze dry) | | | | | | Film | | | | | | Solid (freeze dry) | Film |
| Administration route | | | Sublingual administration | | | | | | | | | | | | | |

<Evaluation 1>

The solutions for transmucosal administration or solid formulations for sublingual administration obtained in the examples and comparative examples were evaluated by the following methods.

solid formulation for sublingual administration (Examples 21 to 32, Comparative Example 3 and 4 (Table 3)) was administered. One week after the administration, the mouse was again anesthetized, and the administration was performed again in the same manner. One week after the second administration, the mouse serum was taken.

(2) ELISA
(Method for Determining Antigen-Specific IgG Titer in Mouse Serum (ELISA))

To each well of a 96-well plate for ELISA was added 100 μL of an OVA-containing solution (100 μg/mL) diluted with carbonate buffer, followed by standing overnight.

The wells were washed three times with preliminarily prepared wash (Tween 20-containing PBS), and to each well was added 200 μL of a blocking solution prepared by diluting a blocking agent (Block Ace, Sumitomo Dainippon Pharma Co., Ltd.) in purified water to 4 g/100 mL. This was followed by standing for 2 hours at room temperature. The wells were then washed three times with wash.

The serum taken from the mouse was centrifuged at 4° C. and 3,000 g for 10 minutes, and the supernatant was recovered. The supernatant was diluted in two-fold increments using a solution prepared by diluting a blocking agent in a phosphate buffer (Nacalai Tesque, Inc.) to 0.4 g/100 mL. The diluted solutions were added to wells (50 μL for each well), followed by standing for 2 hours at room temperature.

The wells were then washed three times with wash. An HRP-labeled anti-mouse IgG antibody (Goat-anti mouse IgG Fc HRP, BETHYL) was diluted 10,000-fold using a solution prepared by diluting a blocking agent in a phosphate buffer (Nacalai Tesque, Inc.) to 0.4 g/100 mL. To each well was added 100 μL of the resulting solution, followed by standing for 1 hour at room temperature.

The wells were then washed three times with wash, and 100 μL of a TMB solution (ELISA POD TMB kit, Nacalai Tesque, Inc.) was added to each well, followed by standing for 30 minutes at dark place.

Thereafter, 100 μL of a 1M sulfuric acid solution was added to each well, and the 96-well plate was subjected to measurement of absorbance at 450 nm with a microplate reader (Spectra Max M2$^e$, Molecular Devices). The IgG titer in the mouse serum was determined as Log 2 titer based on the absorbance at the incremental dilution.

Examples 33 to 42, Comparative Example 5

(Preparation of Cream for Transdermal Administration)

Creams for transdermal administration having a composition shown in Table 4 were prepared. Specifically, an antigen (ovalbumin (OVA), Sigma-Aldrich Co. LLC) and an immunity induction promoter that is a bisphosphonate each in an amount as shown in Table 4 were blended, followed by addition of a base (base cream) thereto in such an amount that the entire amount became 100 parts by weight. The mixture was mixed to give a cream for transdermal administration. The base cream used was prepared by mixing materials in amounts as shown in Table 5.

The immunity induction promoter that is a bisphosphonate used was the same as that used for the preparation of the solution for transnasal or sublingual administration. White Vaseline, sorbitan monostearate, isostearic acid, benzyl alcohol, stearyl alcohol, polysorbate 60, concentrated glycerin, and dimethyl sulfoxide were purchased from Wako Pure Chemical Industries, Ltd. Cetanol was purchased from Tokyo Chemical Industry Co., Ltd.

A PET film/PET nonwoven fabric laminate (area: 0.7 cm$^2$) was attached to an adhesive tape for fixation at a central portion in such a manner that the PET film was in contact with the tape, thereby preparing a complex base. To the nonwoven fabric part of the obtained complex base, 4 mg of each cream for transdermal administration was applied. The resulting product was used as an administration sample in a mouse immunity test.

TABLE 4

| | | | Composition [μg] | | | | | | | | | | |
|---|---|---|---|---|---|---|---|---|---|---|---|---|---|
| | | | Example | | | | | | | | | | Comparative Example |
| Component | | | 33 | 34 | 35 | 36 | 37 | 38 | 39 | 40 | 41 | 42 | 5 |
| Antigen | OVA | | 5 | 5 | 5 | 5 | 5 | 5 | 5 | 5 | 5 | 5 | 5 |
| Immunity induction promoter | Bisphosphonate | Etidronate | 2 | — | — | — | — | — | — | — | — | — | — |
| | | Clodronate | — | 2 | — | — | — | — | — | — | — | — | — |
| | | Tiludronate | — | — | 2 | — | — | — | — | — | — | — | — |
| | | Pamidronate | — | — | — | 2 | — | — | — | — | — | — | — |
| | | Neridronate | — | — | — | — | 1 | — | — | — | — | — | — |
| | | Alendronate | — | — | — | — | — | 1 | — | — | — | — | — |
| | | Ibandronate | — | — | — | — | — | — | 1 | — | — | — | — |
| | | Zoledronate | — | — | — | — | — | — | — | 0.5 | — | — | — |
| | | Risedronate | — | — | — | — | — | — | — | — | 0.5 | — | — |
| | | Minodronate | — | — | — | — | — | — | — | — | — | 0.5 | — |
| Ointment cream (base cream) | | | 93.0 | 93.0 | 93.0 | 93.0 | 94.0 | 94.0 | 94.0 | 94.5 | 94.5 | 94.5 | 95.0 |
| Amount [mg/mouse] | | | 4.0 | 4.0 | 4.0 | 4.0 | 4.0 | 4.0 | 4.0 | 4.0 | 4.0 | 4.0 | 4.0 |
| Dosage form | | | Cream | | | | | | | | | | |
| Administration route | | | Transdermal administration | | | | | | | | | | |

TABLE 5

| | Additive | Amount [parts by weight] |
|---|---|---|
| Base cream | White Vaseline | 60.7 |
| | Sorbitan monostearate | 0.7 |
| | Isostearic acid | 12 |
| | Benzyl alcohol | 2.4 |
| | Cetanol | 2.4 |
| | Stearyl alcohol | 3.5 |
| | Polysorbate 60 | 3.5 |
| | Concentrated glycerin | 2.4 |
| | Purified water | 12.4 |
| | Total | 100 |

<Evaluation 2>

The creams for transdermal administration obtained in the examples and comparative examples were evaluated by the following methods.

(Evaluation of the Humoral Immunity Inducing Effect)

Figure 4:
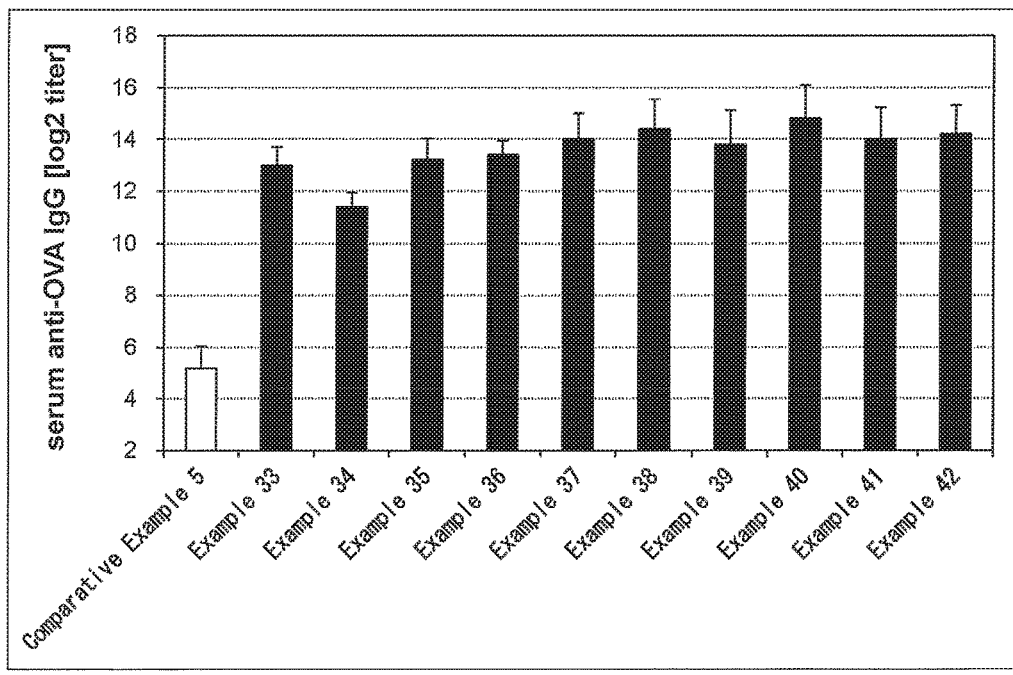
FIG. 4 is a graph showing antigen (OVA)-specific IgG titers in mouse serums after transdermal administration of creams for transdermal administration obtained in examples and comparative examples.

In accordance with the following procedure, a mouse immunity test using an animal model for immunological evaluation was performed with the cream for transdermal administration. Then, the antigen (OVA)-specific IgG antibody in the mouse serum was analyzed for evaluation of the systemic immune response. FIG. 4 shows the evaluation results.

(1) Mouse Immunity Test of Cream for Transdermal Administration

The right back of a mouse (C57BL6 NCr mouse, female, 7 weeks old) was shaved in advance. After a rearing period for recovery from the skin damage caused by the shaving, 4 mg of the cream for transdermal administration was administered to the skin of the right back, and the left back was shaved at the same time. Twenty-four hours later, the cream for transdermal administration on the right back was removed. One week after the administration, the cream for transdermal administration was similarly administered to the skin of the left back of the mouse and removed 24 hours later. One week after the second administration, the mouse serum was taken.

(2) ELISA

The antigen (OVA)-specific IgG antibody in the mouse serum was analyzed by ELISA by the same procedure as in <Evaluation 1>, the evaluation of the solution for transmucosal administration or the solid formulation for sublingual administration.

Examples 43 to 162, Comparative Examples 6 to 45

Solutions for transmucosal administration (transnasal administration or sublingual administration) having a composition as shown in Tables 6 to 10 were prepared. Specifically, an antigen and an immunity induction promoter that is a bisphosphonate were blended in amounts specified in Tables 6 to 10. For transnasal administration, saline was added thereto such that the amount of the resulting mixture was 10 µL. For sublingual administration, saline was added such that the amount of the resulting mixture was 30 µL. This was followed by mixing to provide a solution for transmucosal administration (transnasal administration or sublingual administration).

Influenza vaccine antigens used were an influenza vaccine antigen-containing solution H1N1 (A/California/07/2009, The Research Foundation for Microbial Diseases of Osaka University), H3N2 (A/Victoria361/2011, The Research Foundation for Microbial Diseases of Osaka University), Influenza B virus (B/Wisconsin/1/2010, The Research Foundation for Microbial Diseases of Osaka University), and Influenza B virus (B/Brisbane/60/2008, The Research Foundation for Microbial Diseases of Osaka University). Also used were a pneumococcal capsular polysaccharide-containing solution (Pneumovax NP, MSD), a HPV16 recombinant protein-containing solution (HPV16, PROSPEC), a live attenuated rotavirus-containing solution (RotaTeq Oral Solution, MSD), an inactivated poliovirus-containing solution (IMOVAX POLIO for subcutaneous injection, Sanofi), an inactivated hepatitis A virus-containing solution (Aimmugen, The Chemo-Sero-Therapeutic Research Institute), an inactivated Japanese encephalitis virus-containing solution (Encevac for subcutaneous injection, The Chemo-Sero-Therapeutic Research Institute), a live attenuated mumps virus-containing solution (live mumps vaccine, Kitasato Daiichi Sankyo Vaccine Co., Ltd), a live attenuated measles virus-containing solution (live measles vaccine, Kitasato Daiichi Sankyo Vaccine Co., Ltd), a live attenuated rubella virus-containing solution (dried live attenuated rubella vaccine, Kitasato Daiichi Sankyo Vaccine Co., Ltd), a solution containing *Haemophilus influenzae* type b polysaccharide-tetanus toxoid conjugate (ActHIB, Sanofi), a recombinant HBs antigen protein-containing solution (Bimmugen, The Chemo-Sero-Therapeutic Research Institute), a live attenuated yellow fever virus-containing solution (yellow fever vaccine, Sanofi), a tetanus toxoid-containing solution (tetanus toxoid, Denka Seiken Co., Ltd.), a live attenuated varicella virus-containing solution (dried live attenuated varicella vaccine, The Research Foundation for Microbial Diseases of Osaka University), a live BCG-containing solution (dried BCG vaccine, Japan BCG Laboratory), and an inactivated rabies virus-containing solution (tissue-cultured inactivated rabies vaccine, The Chemo-Sero-Therapeutic Research Institute).

As the immunity induction promoter that is a bisphosphonate, etidronate (LKT Laboratories, Inc.), alendronate (medichem), and zoledronate (Konan Chemical Industry co., ltd.) were used.

Examples 163 to 172, Comparative Example 46

Creams for transdermal administration having a composition shown in Table 11 were prepared in the same manner as in the case of the creams for transdermal administration shown in Table 4. A mouse (C57BL6 NCr mouse, female, 7 weeks old) was prepared and its right back was shaved. Corneum exfoliation treatment was performed thereon five times using an OPP tape (EZ Dunplon No. 3301EZ) produced by Nitto Denko Corporation. The cream (4 mg) was administered to the treated skin (minimally invasive administration), and the left back of the mouse was shaved at the same time. Twenty-four hours later, the cream for transdermal administration on the right back was removed. One week after the administration, corneum exfoliation treatment was similarly performed on the skin of the left back of the mouse. The cream for transdermal administration was administered and removed 24 hours later. One week after the second administration, the mouse serum was taken. The antigen (OVA)-specific IgG antibody in the mouse serum was analyzed by ELISA.

<Evaluation 3>

The solutions for transmucosal administration obtained in the examples and comparative examples were evaluated by the following methods.

(Evaluation of the Humoral Immunity Inducing Effect)

A mouse immunity test using an animal model for immunological evaluation was performed with the solution for transmucosal administration by the following procedure. Then, the systemic immune response was evaluated by analyzing the antigen-specific IgG antibody in the mouse serum.

(1) Mouse Immunity Test of Solution for Transmucosal Administration

Mouse serum was taken by the same procedure as in <Evaluation 1>, evaluation of the solutions for transmucosal administration or solid formulations for sublingual administration.

(2) ELISA

The antigen-specific IgG antibody in the mouse serum was analyzed by ELISA by the same procedure as in <Evaluation 1>, evaluation of the solutions for transmucosal administration or solid formulations for sublingual administration.

The evaluation of the humoral immunity inducing effect shows that the transmucosal administration (transnasal administration or sublingual administration) of a solution for transmucosal administration containing an immunity induction promoter that is a bisphosphonate (Examples 43 to 162) provides a higher antigen-specific IgG titer than the administration of a solution for transmucosal administration free from an immunity induction promoter that is a bisphosphonate (Comparative Examples 6 to 45).

Accordingly, also when antigens such as those shown in Tables 6 to 10 below are used, the use of an immunity induction promoter that is a bisphosphonate leads to a high antigen-specific IgG titer.

Also in the case of an immunization method by minimally invasive administration as shown in Table 11, the humoral immunity specific to the administered antigen can be induced.

TABLE 6

| | Antigen | | Immunity induction promoter | | | | |
|---|---|---|---|---|---|---|---|
| | Name | Amount [μg] | Bisphosphonate | Amount [μg] | Dosage form | Administration route | Amount [μL] |
| Comparative Example 6 | A/California/07/2009 [H1N1] | 1.0 | — | — | Solution | Transnasal | 10 |
| Example 43 | A/California/07/2009 [H1N1] | 1.0 | Etidronate | 10 | Solution | Transnasal | 10 |
| Example 44 | A/California/07/2009 [H1N1] | 1.0 | Alendronate | 10 | Solution | Transnasal | 10 |
| Example 45 | A/California/07/2009 [H1N1] | 1.0 | Zoledronate | 10 | Solution | Transnasal | 10 |
| Comparative Example 7 | A/California/07/2009 [H1N1] | 1.0 | — | — | Solution | Sublingual | 30 |
| Example 46 | A/California/07/2009 [H1N1] | 1.0 | Etidronate | 100 | Solution | Sublingual | 30 |
| Example 47 | A/California/07/2009 [H1N1] | 1.0 | Alendronate | 50 | Solution | Sublingual | 30 |
| Example 48 | A/California/07/2009 [H1N1] | 1.0 | Zoledronate | 50 | Solution | Sublingual | 30 |
| Comparative Example 8 | A/Victoria361/2011 [H3N2] | 1.0 | — | — | Solution | Transnasal | 10 |
| Example 49 | A/Victoria361/2011 [H3N2] | 1.0 | Etidronate | 10 | Solution | Transnasal | 10 |
| Example 50 | A/Victoria361/2011 [H3N2] | 1.0 | Alendronate | 10 | Solution | Transnasal | 10 |
| Example 51 | A/Victoria361/2011 [H3N2] | 1.0 | Zoledronate | 10 | Solution | Transnasal | 10 |
| Comparative Example 9 | A/Victoria361/2011 [H3N2] | 1.0 | — | — | Solution | Sublingual | 30 |
| Example 52 | A/Victoria361/2011 [H3N2] | 1.0 | Etidronate | 100 | Solution | Sublingual | 30 |
| Example 53 | A/Victoria361/2011 [H3N2] | 1.0 | Alendronate | 50 | Solution | Sublingual | 30 |
| Example 54 | A/Victoria361/2011 [H3N2] | 1.0 | Zoledronate | 50 | Solution | Sublingual | 30 |
| Comparative Example 10 | B/Wisconsin/1/2010 | 1.0 | — | — | Solution | Transnasal | 10 |
| Example 55 | B/Wisconsin/1/2010 | 1.0 | Etidronate | 10 | Solution | Transnasal | 10 |
| Example 56 | B/Wisconsin/1/2010 | 1.0 | Alendronate | 10 | Solution | Transnasal | 10 |
| Example 57 | B/Wisconsin/1/2010 | 1.0 | Zoledronate | 10 | Solution | Transnasal | 10 |
| Comparative Example 11 | B/Wisconsin/1/2010 | 1.0 | — | — | Solution | Sublingual | 30 |
| Example 58 | B/Wisconsin/1/2010 | 1.0 | Etidronate | 100 | Solution | Sublingual | 30 |
| Example 59 | B/Wisconsin/1/2010 | 1.0 | Alendronate | 50 | Solution | Sublingual | 30 |
| Example 60 | B/Wisconsin/1/2010 | 1.0 | Zoledronate | 50 | Solution | Sublingual | 30 |
| Comparative Example 12 | B/Brisbane/60/2008 | 1.0 | — | — | Solution | Transnasal | 10 |
| Example 61 | B/Brisbane/60/2008 | 1.0 | Etidronate | 10 | Solution | Transnasal | 10 |
| Example 62 | B/Brisbane/60/2008 | 1.0 | Alendronate | 10 | Solution | Transnasal | 10 |
| Example 63 | B/Brisbane/60/2008 | 1.0 | Zoledronate | 10 | Solution | Transnasal | 10 |
| Comparative Example 13 | B/Brisbane/60/2008 | 1.0 | — | — | Solution | Sublingual | 30 |
| Example 64 | B/Brisbane/60/2008 | 1.0 | Etidronate | 100 | Solution | Sublingual | 30 |
| Example 65 | B/Brisbane/60/2008 | 1.0 | Alendronate | 50 | Solution | Sublingual | 30 |
| Example 66 | B/Brisbane/60/2008 | 1.0 | Zoledronate | 50 | Solution | Sublingual | 30 |

TABLE 7

| | Antigen | | Immunity induction promoter | | | | |
|---|---|---|---|---|---|---|---|
| | Name | Amount [μg] | Bisphosphonate | Amount [μg] | Dosage form | Administration route | Amount [μL] |
| Comparative Example 14 | Pneumococcal capsular polysaccharide Pneumovax NP | 20 | — | — | Solution | Transnasal | 10 |
| Example 67 | Pneumococcal capsular polysaccharide Pneumovax NP | 20 | Etidronate | 10 | Solution | Transnasal | 10 |
| Example 68 | Pneumococcal capsular polysaccharide Pneumovax NP | 20 | Alendronate | 10 | Solution | Transnasal | 10 |
| Example 69 | Pneumococcal capsular polysaccharide Pneumovax NP | 20 | Zoledronate | 10 | Solution | Transnasal | 10 |
| Comparative Example 15 | Pneumococcal capsular polysaccharide Pneumovax NP | 20 | — | — | Solution | Sublingual | 30 |
| Example 70 | Pneumococcal capsular polysaccharide Pneumovax NP | 20 | Etidronate | 100 | Solution | Sublingual | 30 |
| Example 71 | Pneumococcal capsular polysaccharide Pneumovax NP | 20 | Alendronate | 50 | Solution | Sublingual | 30 |
| Example 72 | Pneumococcal capsular polysaccharide Pneumovax NP | 20 | Zoledronate | 50 | Solution | Sublingual | 30 |
| Comparative Example 16 | HPV16 recombinant protein | 10 | — | — | Solution | Transnasal | 10 |
| Example 73 | HPV16 recombinant protein | 10 | Etidronate | | Solution | Transnasal | 10 |

TABLE 7-continued

| | Antigen | | Immunity induction promoter | | Dosage form | Administration route | Amount [μL] |
|---|---|---|---|---|---|---|---|
| | Name | Amount [μg] | Bisphosphonate | Amount [μg] | | | |
| Example 74 | HPV16 recombinant protein | 10 | Alendronate | 10 | Solution | Transnasal | 10 |
| Example 75 | HPV16 recombinant protein | 10 | Zoledronate | 10 | Solution | Transnasal | 10 |
| Comparative Example 17 | HPV16 recombinant protein | 10 | — | — | Solution | Sublingual | 30 |
| Example 76 | HPV16 recombinant protein | 10 | Etidronate | 100 | Solution | Sublingual | 30 |
| Example 77 | HPV16 recombinant protein | 10 | Alendronate | 50 | Solution | Sublingual | 30 |
| Example 78 | HPV16 recombinant protein | 10 | Zoledronate | 50 | Solution | Sublingual | 30 |
| Comparative Example 18 | Live attenuated rotavirus (RIX4414 strain) | 10 | — | — | Solution | Transnasal | 10 |
| Example 79 | Live attenuated rotavirus (RIX4414 strain) | 10 | Etidronate | 10 | Solution | Transnasal | 10 |
| Example 80 | Live attenuated rotavirus (RIX4414 strain) | 10 | Alendronate | 10 | Solution | Transnasal | 10 |
| Example 81 | Live attenuated rotavirus (RIX4414 strain) | 10 | Zoledronate | 10 | Solution | Transnasal | 10 |
| Comparative Example 19 | Live attenuated rotavirus (RIX4414 strain) | 10 | — | — | Solution | Sublingual | 30 |
| Example 82 | Live attenuated rotavirus (RIX4414 strain) | 10 | Etidronate | 100 | Solution | Sublingual | 30 |
| Example 83 | Live attenuated rotavirus (RIX4414 strain) | 10 | Alendronate | 50 | Solution | Sublingual | 30 |
| Example 84 | Live attenuated rotavirus (RIX4414 strain) | 10 | Zoledronate | 50 | Solution | Sublingual | 30 |
| Comparative Example 20 | Inactivated poliovirus (type 1, type 2, type 3) | Vaccine 100 μL equivalent | — | — | Solution | Transnasal | 10 |
| Example 85 | Inactivated poliovirus (type 1, type 2, type 3) | Vaccine 100 μL equivalent | Etidronate | 10 | Solution | Transnasal | 10 |
| Example 86 | Inactivated poliovirus (type 1, type 2, type 3) | Vaccine 100 μL equivalent | Alendronate | 10 | Solution | Transnasal | 10 |
| Example 87 | Inactivated poliovirus (type 1, type 2, type 3) | Vaccine 100 μL equivalent | Zoledronate | 10 | Solution | Transnasal | 10 |
| Comparative Example 21 | Inactivated poliovirus (type 1, type 2, type 3) | Vaccine 100 μL equivalent | — | — | Solution | Sublingual | 30 |
| Example 88 | Inactivated poliovirus (type 1, type 2, type 3) | Vaccine 100 μL equivalent | Etidronate | 100 | Solution | Sublingual | 30 |
| Example 89 | Inactivated poliovirus (type 1, type 2, type 3) | Vaccine 100 μL equivalent | Alendronate | 50 | Solution | Sublingual | 30 |
| Example 90 | Inactivated poliovirus (type 1, type 2, type 3) | Vaccine 100 μL equivalent | Zoledronate | 50 | Solution | Sublingual | 30 |

TABLE 8

| | Antigen | | Immunity induction promoter | | Dosage form | Administration route | Amount [μL] |
|---|---|---|---|---|---|---|---|
| | Name | Amount [μg] | Bisphosphonate | Amount [μg] | | | |
| Comparative Example 22 | Inactivated hepatitis A virus | Vaccine 100 μL equivalent | — | — | Solution | Transnasal | 10 |
| Example 91 | Inactivated hepatitis A virus | Vaccine 100 μL equivalent | Etidronate | 10 | Solution | Transnasal | 10 |
| Example 92 | Inactivated hepatitis A virus | Vaccine 100 μL equivalent | Alendronate | 10 | Solution | Transnasal | 10 |
| Example 93 | Inactivated hepatitis A virus | Vaccine 100 μL equivalent | Zoledronate | 10 | Solution | Transnasal | 10 |
| Comparative Example 23 | Inactivated hepatitis A virus | Vaccine 100 μL equivalent | — | — | Solution | Sublingual | 30 |
| Example 94 | Inactivated hepatitis A virus | Vaccine 100 μL equivalent | Etidronate | 100 | Solution | Sublingual | 30 |
| Example 95 | Inactivated hepatitis A virus | Vaccine 100 μL equivalent | Alendronate | 50 | Solution | Sublingual | 30 |
| Example 96 | Inactivated hepatitis A virus | Vaccine 100 μL equivalent | Zoledronate | 50 | Solution | Sublingual | 30 |
| Comparative Example 24 | Inactivated Japanese encephalitis virus | Vaccine 100 μL equivalent | — | — | Solution | Transnasal | 10 |
| Example 97 | Inactivated Japanese encephalitis virus | Vaccine 100 μL equivalent | Etidronate | 10 | Solution | Transnasal | 10 |
| Example 98 | Inactivated Japanese encephalitis virus | Vaccine 100 μL equivalent | Alendronate | 10 | Solution | Transnasal | 10 |
| Example 99 | Inactivated Japanese encephalitis virus | Vaccine 100 μL equivalent | Zoledronate | 10 | Solution | Transnasal | 10 |
| Comparative Example 25 | Inactivated Japanese encephalitis virus | Vaccine 100 μL equivalent | — | — | Solution | Sublingual | 30 |
| Example 100 | Inactivated Japanese encephalitis virus | Vaccine 100 μL equivalent | Etidronate | 100 | Solution | Sublingual | 30 |
| Example 101 | Inactivated Japanese encephalitis virus | Vaccine 100 μL equivalent | Alendronate | 50 | Solution | Sublingual | 30 |
| Example 102 | Inactivated Japanese encephalitis virus | Vaccine 100 μL equivalent | Zoledronate | 50 | Solution | Sublingual | 30 |
| Comparative Example 26 | Live attenuated mumps virus | Vaccine 100 μL equivalent | — | — | Solution | Transnasal | 10 |
| Example 103 | Live attenuated mumps virus | Vaccine 100 μL equivalent | Etidronate | 10 | Solution | Transnasal | 10 |
| Example 104 | Live attenuated mumps virus | Vaccine 100 μL equivalent | Alendronate | 10 | Solution | Transnasal | 10 |
| Example 105 | Live attenuated mumps virus | Vaccine 100 μL equivalent | Zoledronate | 10 | Solution | Transnasal | 10 |
| Comparative Example 27 | Live attenuated mumps virus | Vaccine 100 μL equivalent | — | — | Solution | Sublingual | 30 |
| Example 106 | Live attenuated mumps virus | Vaccine 100 μL equivalent | Etidronate | 100 | Solution | Sublingual | 30 |
| Example 107 | Live attenuated mumps virus | Vaccine 100 μL equivalent | Alendronate | 50 | Solution | Sublingual | 30 |
| Example 108 | Live attenuated mumps virus | Vaccine 100 μL equivalent | Zoledronate | 50 | Solution | Sublingual | 30 |
| Comparative Example 28 | Live attenuated measles virus | Vaccine 100 μL equivalent | — | — | Solution | Transnasal | 10 |
| Example 109 | Live attenuated measles virus | Vaccine 100 μL equivalent | Etidronate | 10 | Solution | Transnasal | 10 |
| Example 110 | Live attenuated measles virus | Vaccine 100 μL equivalent | Alendronate | 10 | Solution | Transnasal | 10 |

TABLE 8-continued

| | Antigen | | Immunity induction promoter | | | | |
|---|---|---|---|---|---|---|---|
| | Name | Amount [μg] | Bisphosphonate | Amount [μg] | Dosage form | Administration route | Amount [μL] |
| Example 111 | Live attenuated measles virus | Vaccine 100 μL equivalent | Zoledronate | 10 | Solution | Transnasal | 10 |
| Comparative Example 29 | Live attenuated measles virus | Vaccine 100 μL equivalent | — | — | Solution | Sublingual | 30 |
| Example 112 | Live attenuated measles virus | Vaccine 100 μL equivalent | Etidronate | 100 | Solution | Sublingual | 30 |
| Example 113 | Live attenuated measles virus | Vaccine 100 μL equivalent | Alendronate | 50 | Solution | Sublingual | 30 |
| Example 114 | Live attenuated measles virus | Vaccine 100 μL equivalent | Zoledronate | 50 | Solution | Sublingual | 30 |

TABLE 9

| | Antigen | | Immunity induction promoter | | | | |
|---|---|---|---|---|---|---|---|
| | Name | Amount [μg] | Bis-phosphonate | Amount [μg] | Dosage form | Administration route | Amount [μL] |
| Comparative Example 30 | Live attenuated rubella virus | Vaccine 100 μL equivalent | — | — | Solution | Transnasal | 10 |
| Example 115 | Live attenuated rubella virus | Vaccine 100 μL equivalent | Etidronate | 10 | Solution | Transnasal | 10 |
| Example 116 | Live attenuated rubella virus | Vaccine 100 μL equivalent | Alendronate | 10 | Solution | Transnasal | 10 |
| Example 117 | Live attenuated rubella virus | Vaccine 100 μL equivalent | Zoledronate | 10 | Solution | Transnasal | 10 |
| Comparative Example 31 | Live attenuated rubella virus | Vaccine 100 μL equivalent | — | — | Solution | Sublingual | 30 |
| Example 118 | Live attenuated rubella virus | Vaccine 100 μL equivalent | Etidronate | 100 | Solution | Sublingual | 30 |
| Example 119 | Live attenuated rubella virus | Vaccine 100 μL equivalent | Alendronate | 50 | Solution | Sublingual | 30 |
| Example 120 | Live attenuated rubella virus | Vaccine 100 μL equivalent | Zoledronate | 50 | Solution | Sublingual | 30 |
| Comparative Example 32 | Haemophilus influenzae type b polysaccharide-tetanus toxoid conjugate | Vaccine 100 μL equivalent | — | — | Solution | Transnasal | 10 |
| Example 121 | Haemophilus influenzae type b polysaccharide-tetanus toxoid conjugate | Vaccine 100 μL equivalent | Etidronate | 10 | Solution | Transnasal | 10 |
| Example 122 | Haemophilus influenzae type b polysaccharide-tetanus toxoid conjugate | Vaccine 100 μL equivalent | Alendronate | 10 | Solution | Transnasal | 10 |
| Example 123 | Haemophilus influenzae type b polysaccharide-tetanus toxoid conjugate | Vaccine 100 μL equivalent | Zoledronate | 10 | Solution | Transnasal | 10 |
| Comparative Example 33 | Haemophilus influenzae type b polysaccharide-tetanus toxoid conjugate | Vaccine 100 μL equivalent | — | — | Solution | Sublingual | 30 |
| Example 124 | Haemophilus influenzae type b polysaccharide-tetanus toxoid conjugate | Vaccine 100 μL equivalent | Etidronate | 100 | Solution | Sublingual | 30 |
| Example 125 | Haemophilus influenzae type b polysaccharide-tetanus toxoid conjugate | Vaccine 100 μL equivalent | Alendronate | 50 | Solution | Sublingual | 30 |
| Example 126 | Haemophilus influenzae type b polysaccharide-tetanus toxoid conjugate | Vaccine 100 μL equivalent | Zoledronate | 50 | Solution | Sublingual | 30 |
| Comparative Example 34 | Recombinant HBs antigen protein | Vaccine 100 μL equivalent | — | — | Solution | Transnasal | 10 |
| Example 127 | Recombinant HBs antigen protein | Vaccine 100 μL equivalent | Etidronate | 10 | Solution | Transnasal | 10 |
| Example 128 | Recombinant HBs antigen protein | Vaccine 100 μL equivalent | Alendronate | 10 | Solution | Transnasal | 10 |
| Example 129 | Recombinant HBs antigen protein | Vaccine 100 μL equivalent | Zoledronate | 10 | Solution | Transnasal | 10 |
| Comparative Example 35 | Recombinant HBs antigen protein | Vaccine 100 μL equivalent | — | — | Solution | Sublingual | 30 |
| Example 130 | Recombinant HBs antigen protein | Vaccine 100 μL equivalent | Etidronate | 100 | Solution | Sublingual | 30 |
| Example 131 | Recombinant HBs antigen protein | Vaccine 100 μL equivalent | Alendronate | 50 | Solution | Sublingual | 30 |
| Example 132 | Recombinant HBs antigen protein | Vaccine 100 μL equivalent | Zoledronate | 50 | Solution | Sublingual | 30 |
| Comparative Example 36 | Live attenuated yellow fever virus | Vaccine 100 μL equivalent | — | — | Solution | Transnasal | 10 |
| Example 133 | Live attenuated yellow fever virus | Vaccine 100 μL equivalent | Etidronate | 10 | Solution | Transnasal | 10 |
| Example 134 | Live attenuated yellow fever virus | Vaccine 100 μL equivalent | Alendronate | 10 | Solution | Transnasal | 10 |
| Example 135 | Live attenuated yellow fever virus | Vaccine 100 μL equivalent | Zoledronate | 10 | Solution | Transnasal | 10 |
| Comparative Example 37 | Live attenuated yellow fever virus | Vaccine 100 μL equivalent | — | — | Solution | Sublingual | 30 |
| Example 136 | Live attenuated yellow fever virus | Vaccine 100 μL equivalent | Etidronate | 100 | Solution | Sublingual | 30 |
| Example 137 | Live attenuated yellow fever virus | Vaccine 100 μL equivalent | Alendronate | 50 | Solution | Sublingual | 30 |
| Example 138 | Live attenuated yellow fever virus | Vaccine 100 μL equivalent | Zoledronate | 50 | Solution | Sublingual | 30 |

TABLE 10

| | Antigen | | Immunity induction promoter | | | | |
|---|---|---|---|---|---|---|---|
| | Name | Amount [μg] | Bisphosphonate | Amount [μg] | Dosage form | Administration route | Amount [μL] |
| Comparative Example 38 | Tetanus toxoid | Vaccine 100 μL equivalent | — | — | Solution | Transnasal | 10 |
| Example 139 | Tetanus toxoid | Vaccine 100 μL equivalent | Etidronate | 10 | Solution | Transnasal | 10 |
| Example 140 | Tetanus toxoid | Vaccine 100 μL equivalent | Alendronate | 10 | Solution | Transnasal | 10 |
| Example 141 | Tetanus toxoid | Vaccine 100 μL equivalent | Zoledronate | 10 | Solution | Transnasal | 10 |
| Comparative Example 39 | Tetanus toxoid | Vaccine 100 μL equivalent | — | — | Solution | Sublingual | 30 |
| Example 142 | Tetanus toxoid | Vaccine 100 μL equivalent | Etidronate | 100 | Solution | Sublingual | 30 |
| Example 143 | Tetanus toxoid | Vaccine 100 μL equivalent | Alendronate | 50 | Solution | Sublingual | 30 |
| Example 144 | Tetanus toxoid | Vaccine 100 μL equivalent | Zoledronate | 50 | Solution | Sublingual | 30 |
| Comparative Example 40 | Live attenuated varicella virus | Vaccine 100 μL equivalent | — | — | Solution | Transnasal | 10 |
| Example 145 | Live attenuated varicella virus | Vaccine 100 μL equivalent | Etidronate | 10 | Solution | Transnasal | 10 |
| Example 146 | Live attenuated varicella virus | Vaccine 100 μL equivalent | Alendronate | 10 | Solution | Transnasal | 10 |
| Example 147 | Live attenuated varicella virus | Vaccine 100 μL equivalent | Zoledronate | 10 | Solution | Transnasal | 10 |
| Comparative Example 41 | Live attenuated varicella virus | Vaccine 100 μL equivalent | — | — | Solution | Sublingual | 30 |
| Example 148 | Live attenuated varicella virus | Vaccine 100 μL equivalent | Etidronate | 100 | Solution | Sublingual | 30 |
| Example 149 | Live attenuated varicella virus | Vaccine 100 μL equivalent | Alendronate | 50 | Solution | Sublingual | 30 |
| Example 150 | Live attenuated varicella virus | Vaccine 100 μL equivalent | Zoledronate | 50 | Solution | Sublingual | 30 |
| Comparative Example 42 | Live BCG | Vaccine 30 μL equivalent | — | — | Solution | Transnasal | 10 |
| Example 151 | Live BCG | Vaccine 30 μL equivalent | Etidronate | 10 | Solution | Transnasal | 10 |
| Example 152 | Live BCG | Vaccine 30 μL equivalent | Alendronate | 10 | Solution | Transnasal | 10 |
| Example 153 | Live BCG | Vaccine 30 μL equivalent | Zoledronate | 10 | Solution | Transnasal | 10 |
| Comparative Example 43 | Live BCG | Vaccine 30 μL equivalent | — | — | Solution | Sublingual | 30 |
| Example 154 | Live BCG | Vaccine 30 μL equivalent | Etidronate | 100 | Solution | Sublingual | 30 |
| Example 155 | Live BCG | Vaccine 30 μL equivalent | Alendronate | 50 | Solution | Sublingual | 30 |
| Example 156 | Live BCG | Vaccine 30 μL equivalent | Zoledronate | 50 | Solution | Sublingual | 30 |
| Comparative Example 44 | Inactivated rabies virus | Vaccine 200 μL equivalent | — | — | Solution | Transnasal | 10 |
| Example 157 | Inactivated rabies virus | Vaccine 200 μL equivalent | Etidronate | 10 | Solution | Transnasal | 10 |
| Example 158 | Inactivated rabies virus | Vaccine 200 μL equivalent | Alendronate | 10 | Solution | Transnasal | 10 |
| Example 159 | Inactivated rabies virus | Vaccine 200 μL equivalent | Zoledronate | 10 | Solution | Transnasal | 10 |
| Comparative Example 45 | Inactivated rabies virus | Vaccine 200 μL equivalent | — | — | Solution | Sublingual | 30 |
| Example 160 | Inactivated rabies virus | Vaccine 200 μL equivalent | Etidronate | 100 | Solution | Sublingual | 30 |
| Example 161 | Inactivated rabies virus | Vaccine 200 μL equivalent | Alendronate | 50 | Solution | Sublingual | 30 |
| Example 162 | Inactivated rabies virus | Vaccine 200 μL equivalent | Zoledronate | 50 | Solution | Sublingual | 30 |

TABLE 11

| | | | Composition [parts by weight] | | | | | | | | | | |
|---|---|---|---|---|---|---|---|---|---|---|---|---|---|
| | | | Example | | | | | | | | | | Comparative Example |
| Component | | | 163 | 164 | 165 | 166 | 167 | 168 | 169 | 170 | 171 | 172 | 46 |
| Antigen | OVA | | 5 | 5 | 5 | 5 | 5 | 5 | 5 | 5 | 5 | 5 | 5 |
| Immunostimulant | Bisphosphonate | Etidronate | 2 | — | — | — | — | — | — | — | — | — | — |
| | | Clodronate | — | 2 | — | — | — | — | — | — | — | — | — |
| | | Tiludronate | — | — | 2 | — | — | — | — | — | — | — | — |
| | | Pamidronate | — | — | — | 2 | — | — | — | — | — | — | — |
| | | Neridronate | — | — | — | — | 1 | — | — | — | — | — | — |
| | | Alendronate | — | — | — | — | — | 1 | — | — | — | — | — |
| | | Ibandronate | — | — | — | — | — | — | 1 | — | — | — | — |
| | | Zoledronate | — | — | — | — | — | — | — | 0.5 | — | — | — |
| | | Risedronate | — | — | — | — | — | — | — | — | 0.5 | — | — |
| | | Minodronate | — | — | — | — | — | — | — | — | — | 0.5 | — |
| Ointment cream (base cream) | | | 93.0 | 93.0 | 93.0 | 93.0 | 94.0 | 94.0 | 94.0 | 94.5 | 94.5 | 94.5 | 95.0 |
| Amount [mg/mouse] | | | 4.0 | 4.0 | 4.0 | 4.0 | 4.0 | 4.0 | 4.0 | 4.0 | 4.0 | 4.0 | 4.0 |
| Dosage form | | | Cream | | | | | | | | | | |
| Administration route | | | Transdermal administration (minimally invasive) | | | | | | | | | | |

INDUSTRIAL APPLICABILITY

The vaccine pharmaceutical composition of the present invention is universally usable for induction of humoral immunity against various antigens, exerts a high antibody production inducing effect, and favorably used for transdermal administration or transmucosal administration.

The invention claimed is:

1. A vaccine pharmaceutical composition for inducing humoral immunity in a subject, comprising:
   an antigen; and
   a bisphosphonate;
   wherein the vaccine pharmaceutical composition is structured and arranged to be administered transdermally and/or transmucosally and, upon administration to the subject, is capable of inducing a humoral immune response in the subject.

2. A method for inducing humoral immunity, comprising transdermally or transmucosally administering to a subject a vaccine pharmaceutical composition comprising:
   an antigen; and
   a bisphosphonate,
   wherein the administration induces a humoral immune response in the subject.

3. The method for inducing humoral immunity according to claim 2, wherein the administering is transdermal.

4. The method for inducing humoral immunity according to claim 2,
   wherein the bisphosphonate is at least one selected from the group consisting of etidronate, clodronate, tiludronate, pamidronate, neridronate, alendronate, ibandronate, zoledronate, risedronate, and minodronate.

5. The method for inducing humoral immunity according to claim 3,
   wherein the bisphosphonate is at least one selected from the group consisting of etidronate, clodronate, tiludronate, pamidronate, neridronate, alendronate, ibandronate, zoledronate, risedronate, and minodronate.

6. The method for inducing humoral immunity according to claim 2, wherein the administering is transmucosal.

7. The method for inducing humoral immunity according to claim 6,
   wherein the bisphosphonate is at least one selected from the group consisting of etidronate, clodronate, tiludronate, pamidronate, neridronate, alendronate, ibandronate, zoledronate, risedronate, and minodronate.

8. The vaccine pharmaceutical composition according to claim 1,
   wherein the bisphosphonate is at least one selected from the group consisting of etidronate, clodronate, tiludronate, pamidronate, neridronate, alendronate, ibandronate, zoledronate, risedronate, and minodronate.

9. The vaccine pharmaceutical composition according to claim 1, wherein the vaccine pharmaceutical composition is structured and arranged to be administered transdermally.

10. The vaccine pharmaceutical composition according to claim 9,
    wherein the bisphosphonate is at least one selected from the group consisting of etidronate, clodronate, tiludronate, pamidronate, neridronate, alendronate, ibandronate, zoledronate, risedronate, and minodronate.

11. The vaccine pharmaceutical composition according to claim 1, which is structured and arranged to be administered transmucosally.

12. The vaccine pharmaceutical composition according to claim 11,
    wherein the bisphosphonate is at least one selected from the group consisting of etidronate, clodronate, tiludronate, pamidronate, neridronate, alendronate, ibandronate, zoledronate, risedronate, and minodronate.

13. The method according to claim 2, wherein the administration is non-invasive.

14. The vaccine pharmaceutical composition according to claim 1, which is structured and arranged to be administered non-invasively.

* * * * *